(12) United States Patent
Tacha

(10) Patent No.: US 10,429,390 B2
(45) Date of Patent: *Oct. 1, 2019

(54) ANTIBODY COCKTAIL SYSTEMS AND METHODS FOR CLASSIFICATION OF HISTOLOGIC SUBTYPES IN LUNG CANCER

(71) Applicant: Biocare Medical LLC, Concord, CA (US)

(72) Inventor: David Tacha, Vacaville, CA (US)

(73) Assignee: Biocare Medical, LLC, Pacheco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,407

(22) PCT Filed: Dec. 18, 2013

(86) PCT No.: PCT/US2013/076203
§ 371 (c)(1),
(2) Date: Jun. 15, 2015

(87) PCT Pub. No.: WO2014/100220
PCT Pub. Date: Jun. 26, 2014

(65) Prior Publication Data
US 2015/0309035 A1 Oct. 29, 2015

Related U.S. Application Data

(60) Provisional application No. 61/738,938, filed on Dec. 18, 2012.

(51) Int. Cl.
*C07K 16/00* (2006.01)
*G01N 33/574* (2006.01)

(52) U.S. Cl.
CPC ... *G01N 33/57423* (2013.01); *G01N 2800/52* (2013.01)

(58) Field of Classification Search
CPC .................................................. C07K 16/00
USPC .................................................... 530/387.1
See application file for complete search history.

(56) References Cited

U.S. PATENT DOCUMENTS

| | | |
|---|---|---|
| 4,145,406 A | 3/1979 | Schick et al. |
| 4,254,082 A | 3/1981 | Schick et al. |
| 4,637,996 A | 1/1987 | Konishi |
| 4,687,732 A | 8/1987 | Ward et al. |
| 4,690,890 A | 9/1987 | Loor et al. |
| 4,792,521 A | 12/1988 | Shochat |
| 4,863,875 A | 9/1989 | Bailey et al. |
| 5,089,423 A | 2/1992 | Diamandis et al. |
| 5,108,896 A | 4/1992 | Philo et al. |
| 5,252,487 A | 10/1993 | Bacus et al. |
| 5,280,108 A | 1/1994 | Fanning |
| 5,482,698 A | 1/1996 | Griffiths |
| 5,487,975 A | 1/1996 | Miller et al. |
| 5,620,845 A | 4/1997 | Gould et al. |
| 5,691,154 A | 11/1997 | Callstrom et al. |
| 5,719,063 A | 2/1998 | Block |
| 5,869,274 A | 2/1999 | Tsao et al. |
| 5,891,658 A | 4/1999 | Klainer et al. |
| 6,008,057 A | 12/1999 | Glass et al. |
| 6,051,693 A | 4/2000 | Handley et al. |
| 6,252,053 B1 | 6/2001 | Ohbayashi et al. |
| 6,409,990 B1 | 6/2002 | Vera |
| 6,476,206 B1 | 11/2002 | Sidransky et al. |
| 6,537,745 B2 | 3/2003 | Chien et al. |
| 6,580,056 B1 | 6/2003 | Tacha |
| 6,723,506 B2 | 4/2004 | Fletcher et al. |
| 6,946,256 B1 | 9/2005 | McKeon et al. |
| 7,354,564 B2 | 4/2008 | Reed |
| 7,422,739 B2 | 9/2008 | Anderson et al. |
| 7,468,425 B2 | 12/2008 | Sidransky et al. |
| 7,674,605 B2 | 3/2010 | Lin et al. |
| 7,785,803 B2 | 8/2010 | Achen et al. |
| 7,846,726 B2 | 12/2010 | Li et al. |
| 7,846,762 B2 | 12/2010 | Rana et al. |
| 7,875,705 B2 | 1/2011 | Iwaneri et al. |
| 7,935,794 B2 | 5/2011 | Pullen |
| 7,935,795 B2 | 5/2011 | Nakajima |
| 7,935,796 B2 | 5/2011 | Lee et al. |
| 7,973,138 B2 | 7/2011 | Liang et al. |
| 8,153,126 B2 | 4/2012 | Violette et al. |
| 8,168,409 B2 | 5/2012 | Calzone et al. |
| 8,338,576 B2 | 12/2012 | Paralkar et al. |

(Continued)

FOREIGN PATENT DOCUMENTS

| | | |
|---|---|---|
| EP | 2402370 A1 | 1/2012 |
| EP | 1733437 B1 | 9/2014 |

(Continued)

OTHER PUBLICATIONS

Nagashio et al (Lung Cancer, 2008, 62: 364-373).*
Yamaguchi et al (Int J Cancer, 2000, 89: 524-528).*
Pelosi et al (Journal of Thoracic Oncology, 2011, 6(6)(sup 2): S335-S336).*
Rekhtman et al (Modern Pathology, 2011, 24: 1348-1359).*
Rossi et al (Am J Clin Pathol, 2005, 124(2): 295-302).*
Zeta Corporation IVD Data Sheet (Rev 052014) p40 (Clone ZR8), 7 pages. Dated Jun. 24, 2015.

(Continued)

*Primary Examiner* — Sean E Aeder
(74) *Attorney, Agent, or Firm* — Santangelo Law Offices, P.C.

(57) ABSTRACT

The present invention relates to compositions and detection systems of antibodies or fragments thereof, wherein at least two antibodies or fragments thereof binds specifically to squamous cell carcinoma (SCC) and/or adenocarcinoma (ADC). Methods for using the antibodies in diagnosis, prognosis, and assessing efficacy of treatment is further included as well as kits including such compositions and detection systems.

7 Claims, 22 Drawing Sheets

(56) References Cited

U.S. PATENT DOCUMENTS

| | | |
|---|---|---|
| 8,603,765 B2 | 12/2013 | Tacha |
| 8,852,592 B2 | 10/2014 | Qi et al. |
| 9,156,915 B2 | 10/2015 | Waldman et al. |
| 9,417,243 B2 | 8/2016 | Qi et al. |
| 9,428,576 B2 | 8/2016 | Tacha et al. |
| 9,429,577 B2 | 8/2016 | Qi et al. |
| 9,442,049 B2 | 9/2016 | Barker et al. |
| 9,708,395 B2 | 7/2017 | Tacha |
| 9,816,997 B2 | 11/2017 | Tacha |
| 9,823,251 B2 | 11/2017 | Qi et al. |
| 10,295,542 B2 | 5/2019 | Tacha et al. |
| 10,316,103 B1 | 6/2019 | Qi et al. |
| 2002/0094547 A1 | 7/2002 | Burstein |
| 2002/0106685 A1 | 8/2002 | Henning et al. |
| 2002/0173053 A1 | 11/2002 | Damaj et al. |
| 2003/0017491 A1 | 1/2003 | Shi et al. |
| 2005/0083802 A1 | 4/2005 | Akahoshi et al. |
| 2005/0186642 A1 | 8/2005 | Tacha |
| 2006/0148063 A1 | 6/2006 | Fauzzi et al. |
| 2007/0015908 A1 | 1/2007 | Fischer et al. |
| 2007/0041972 A1 | 2/2007 | Rather et al. |
| 2008/0267988 A1 | 10/2008 | Calenoff |
| 2009/0000360 A1 | 1/2009 | Ogawa |
| 2009/0191190 A1 | 7/2009 | Barghorn et al. |
| 2010/0004782 A1 | 2/2010 | Tacha |
| 2010/0047825 A1 | 2/2010 | Tacha |
| 2010/0092457 A1 | 4/2010 | Aburatani et al. |
| 2012/0082999 A1 | 4/2012 | Liao et al. |
| 2012/0154983 A1 | 6/2012 | Zhang et al. |
| 2012/0245051 A1 | 9/2012 | Rimm et al. |
| 2012/0321557 A1 | 12/2012 | Kimura |
| 2014/0004542 A1 | 1/2014 | Qi et al. |
| 2014/0057803 A1 | 2/2014 | Tacha |
| 2015/0056635 A1 | 2/2015 | Qi et al. |
| 2015/0152180 A1 | 6/2015 | Davis et al. |
| 2016/0009795 A1 | 1/2016 | Tacha et al. |
| 2016/0216269 A1 | 7/2016 | Tacha et al. |
| 2016/0333085 A1 | 11/2016 | Tacha et al. |
| 2016/0334407 A1 | 11/2016 | Qi et al. |
| 2016/0370370 A1 | 12/2016 | Qi et al. |
| 2018/0074065 A1 | 3/2018 | Tacha et al. |

FOREIGN PATENT DOCUMENTS

| | | |
|---|---|---|
| EP | 2900265 B1 | 5/2018 |
| WO | 9950287 A2 | 10/1999 |
| WO | 2003003906 A1 | 1/2003 |
| WO | 2005054860 A1 | 6/2005 |
| WO | 2005076005 A2 | 8/2005 |
| WO | 2005083802 A1 | 9/2005 |
| WO | 2010017170 A1 | 2/2010 |
| WO | 2010022736 A2 | 3/2010 |
| WO | 2010124689 A1 | 11/2010 |
| WO | 2012031273 A2 | 3/2012 |
| WO | 2012154983 A2 | 11/2012 |
| WO | 2012154983 A3 | 11/2012 |
| WO | 2014052672 A1 | 4/2014 |
| WO | 2014100220 A2 | 6/2014 |
| WO | 2014134587 A1 | 9/2014 |
| WO | 2015051320 A2 | 4/2015 |
| WO | 2015051320 A2 | 8/2016 |

OTHER PUBLICATIONS

European Patent App. No. 14178215.1 Examination Report dated Dec. 15, 2015, 5 pages.

European Patent App. No. 14178215.1 Search Report dated Dec. 1, 2014, 11 pages.

Cartron, et al. Therapeutic activity of humanized anti-DC20 monoclonal antibody and polymorphism in IgG Fc receptor gene. www.bloodjournal.org, Jan. 21, 2016. 6 pages.

Foran, James M. et al. European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma. Journal of Clinical Oncology, vol. 18, No. 2/317; Jan. 1, 2000, 7 pages. Abstract only.

Eng, Hui-Yan, et al. Enhanced antigen detection in immunohistochemical staining using a 'digitized' chimeric antibody. Oxford, Protein Engineering, Design & Selection, 2016, vol. 29 No. 1, pp. 11-21. Sep. 25, 2015, 11 pages.

Carter, Paul J. Potent antibody therapeutics by design. Nature Reviews, Immunology. vol. 6, May 2006. pp. 343-357. 15 pages.

Chames et al. Therapeutic antibodies: success, limitations and hopes for the future. Themed Section: Vector Design and Drug Delivery Review. British Journal of Pharmacology (2009) 157,200-233.

Jakobovits, Aya. Production of fully human antibodies by transgenic mice. Cell Genesys Inc., Foster City, USA. Current Opinion in Biotechnology 1995, 6:561-566.

Kellermann & Green, Antibody discovery: the use of transgenic mice to generate human monoclonal antibodies for therapeutics. Current Opinion in Biotechnology 2002, 13:593-597.

Morrison et al. Chimeric human antibody molecules: Mouse antigen-binding domains with human constant region domains. Proc. Natl. Adad. Sci. USA. vol. 81, pp. 6851-6855, Nov. 1984.

Winter et al. Humanized antibodies. Immunology Today vol. 14 No. 6 1993. 4 pages.

U.S. Appl. No. 15/026,904, filed Apr. 1, 2016. First Inventor: David Tacha.

International Application No. PCT/US14159162; filed Oct. 3, 2014. International Preliminary Report on Patentability, 6 pages, dated Apr. 5, 2016.

European Patent App. No. 13841542.7. Extended European search report dated Apr. 28, 2016. 9 pages.

U.S. Appl. No. 15/222,690, filed Jul. 29, 2016. First Named Inventor: Weimin Qi.

U.S. Appl. No. 15/226,794, filed Aug. 2, 2016. First Named Inventor: Weimin Qi.

U.S. Appl. No. 62/306,517, filed Mar. 10, 2016. First Named Inventor: Jillian Tyrrell.

U.S. Appl. No. 15/008,069, filed Jan. 27, 2016. First Named Inventor: Weimin Qi.

U.S. Appl. No. 15/228,341, filed Aug. 4, 2016. First Named Inventor: David Tacha.

Tacha et al. "A Newly Developed Mouse Monoclonal SOX10 Antibody is a Highly Sensitive and Specifica Marker for Malignant Melanoma, Including Spindle Cell and Desmoplastic Melanomas" Archives of Pathology & Laboratory Medicine: Apr. 2015, vol. 139, No. 4, pp. 530-536; Epub Dec. 1, 2014; doi: http://dx.doi.org/10.5858/arpa.2014-0077-OA.

Harlow, E. and Lane, D., Antibodies: A Laboratory Manual (1988) Cold Spring Harbor Laboratory Press, Cold Spring Harbor, NY, pp. 23-24 and 72-76.

Van Regenmortel et al. "Molecular dissectinon of protein anitgens and the prediction of epitopes", Chaper 1 in: Laboratory Techniques in Biochemistry and molecular Biology vol. 19, 1988, pp. 1-39.

Kuby et al. Immunology, W.H. Freeman and Company (1992), p. 125.

Bost et al., "Antibodies against a peptide sequence within ght HIV envelope protein crossreacts with human interleukin-2" Immunol. Invest. 1988; 17:577-586.

Bendayan, M. "Possibilites of false immunocytochemical results generated by the use of monoclonal antibodies: the example of the anti-proinsulin" J. Histochem Ctyochem 1995; 43:881-886.

Zhou, Ming. al., "Basal Cell Cocktail (34βE12+p63) Improves the Detection of Prostate Basal Cells", Am. J. Surg. Path., 2003: 27(3), 365-371.

Zhou, Ming et al., "Expression and Disgnostic Utility of Alpha-Methylacyl-CoA-Racemase (P504S) in Foamy Gland and Pseudohyperplastic Prostate Cancer", Am. J. Surgical Pathology 27(6): 772-778, 2003.

Anonymous: "PIN cocktail-2 (P504S+p63)", Biocarta. May 4, 2003, pp. 1-2. XP002667408, Retrieved from the Internet: URL:http://www.biocarta.com/TDS/PM205DSH.pdf [retrieved on Jan. 18, 2012].

Anonymous: "Double vision. The double stain, polymer detection system", Biocare Medical, Aug. 2, 2003, pp. 1-3, XP002667409,

(56) References Cited

OTHER PUBLICATIONS retrieved from the Internet: URL: htt12 ://web/archive. org/web/20030802112943/httQ :1/biocare. net/Detection. htm [retrieved Jan. 18, 2012].

Anonymous: "Double vision, the double stain, polymer detection system", Biocare Medical, Oct. 2, 2003, pp. 1-3, XP002667410, retrieved from the Internet: URL:htt12 ://web/archive .org/web/20031 002060452/httQ ://biocare. net/Detection. htm [retrieved Jan. 18, 2012).

Anonymous: "Double vision, the double stain, polymer detection system", Biocare Medical, Jan. 1, 2004, pp. 1-5, XP002667411, retrieved from the Internet: URL: htt12 ://web/archive .org/web/20040 1 01180833/httQ :1/biocare. net/Detection. htm [retrieved Jan. 18, 2012].

Susan Van Noorden., "Immunocytochemistry for light microscopy a technical update", The biomedical Scientist, XP-002522654, Aug. 2003, pp. 808-811.

Rami Suzuki. et al., "Proliferation and differentiation in the human breast during pregnancy", Differentiation. vol. 66, No. 2-3, XP-002522647, Oct. 2000, pp. 106-115.

BioGenex datasheet, Rabbit Anti-PIN4 Cocktail—AB448ME, Doc. No. 932-448ME Rev A, release date Aug. 17, 2007.

Van der Loos, "Immunoenzyme Multiple Staining Methods", Microscopy Handbooks 45, (1999); Bios Scientific Publishers Ltd: Oxford, UK.

Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.

David Y. Mason, et al., "Double immunofluorescence labelling of routinely processed paraffin sections", Journal of Pathology, vol. 191, No. 4. XP-002522649, Aug. 2000, pp. 452-461.

Susan Van Noorden., "Advances in immunocytochemistry", Folia Histochemica Et Cytobiologica, vol. 40, No. 2, XP-008104795, 2002, pp. 121-124.

Van der Loos, et al., "Immunohistochemical Detection of Interferon-y: Fake or Fact?", The Journal of Histochemistry & Cytochemistry, vol. 49, No. 6, XP-002522653, Jun. 2001. pp. 699-709.

Van der loos. et al. "The Animal Research Kit (ARK} Can Be Used in a Multistep Double Staining Method for Human Tissue Specimens", The Journal of Histochemistry & Cytochemistry, vol. 48, (10}: 1431-1437 (2000).

Van der Loos, et al, "Multiple immunoenzyme staining techniques Use of fluoresceinated, biotinylated and unlabeled monoclonal antibodies", Journal of Immunological Methods, 117 (1989), pp. 45-52.

Van der loos. et al. "An Immunoenzyme Triple-staining Method Using Both Polyclonal and Monoclonal antibodies from the same Species. Application of combined direct, Indirect, and Avidin-Biotin Complex (ABC) Technique", The Journal of Histochemistry and Cytochemistry, vol. 35, No. 11, pp. 1199-1204 (1987).

Van der Loos, et al. "Practical suggestions for successful immunoenzyme double-staining experiments", Histochemical Journal (25), pp. 1-13 (1993).

Brunangelo Falin!, et al., "Double Labeled-Antigen Method for Demonstration of Intracellular Antigens in Paraffin-embedded Tissues", The Journal of Histochemistry and Cytochemistry. vol. 30, No. 1, pp. 21-26 (1982).

Data Sheet Fast Red Stubsrate Pack and Compponents for Use with Alakline Phosphatase Detection Kits & BioGenex Automated Staining Systems (Doc. No. HK180, Rev. No. F112) Jul. 1, 2003 accessed from web.archive.org/web/20030701115828/http://www.bioQenex.com/biOQenex h.html.

Vector Red Alkaline Phosphatase Substrate Kit I Cat. No. SK-5100, Oct. 31, 2000, accessed from web.archive.org/web/20031202200453/http://www.vector.labs.com/protocols.asp.

Cordell et al, Journal of Histochemistry and Cytochemistry, 1984, vol. 32, No. 2 pp. 219-229 attached online version htte://jhc.sageeub.com/content/32/2/219.

Instructions for Universal Alkaline Phosphatase Immunostaining Kit (for Mouse and Rabbit Primary Antibodies) Cat. #KA-50F Apr. 7, 2003 Accessed from web.archive.org/web/20030407222427/http:l/dbiosys.com/new/index.asp?fuse=dsp cat&id=5.

Elias, Immunohistopathology—A Practical Approach to Diagnosis, 2nd Ed. , American Society for Clinical Pathology Press: Chicago, © 2003, p. 36.

Molinie, V. et. al., Mod. Pathol., 2004, 17, 1180.

Paner, GP, . et. al., Best Prac. in Diag. Immunohist.: Prostate, 2008, 132, 1388.

Rubin, MA et. al., JAMA, 2002,287, 1662.

Shah, RB et. al., Am. J. Surg. Path., 2002, 26, 1161.

Signoretti, Sabina 'p63 is a prostate basal cell marker and is required for prostate development'. Am J Pathol, vol. 157, No. 6, Dec. 2000, 1769-75.

Tacha, DE and Miller, RT, Appl. Immunohistochem. Mol. Morph .. 2004, 12, 75.

Tavora. F and Epstein, JI, Am. J. Surg. Path., 2008, 32, 1060.

Yang, Yet. al., Am. J. Path., 1997, 150, 693.

Abrahams, NA, et. a f., Histopathology, 2002, 41, 35.

Adley, BP et. al., Am. J. Clin. Path., 2006, 126, 849.

Beach, R et. al., Am. J. Surg. Path., 2002, 26, 1588.

Bostwick, DG and Qian, J., Mod. Pathol., 2004, 17, 360.

DAKO Press Release Sep. 14, 2009, New Duoflex Cocktail Antibodies.

DAKO Screen Shot DuoFlex Cocktail, Anti-AMACR, Anti-Cytokeratin HMW, Anti-Cytoderatin 5/6: Oct. 5, 2009.

Herawi, M and Epstein, JI, Am. J. Surg. Path., 2007, 31, 889.

Jiang, Z et. al., Am. J. Clin. Path., 2004, 122, 275.

Jiang, Z et. al., Am. J. Clin. Path., 2005, 123,231.

Jiang, Z et. al., Am. J. Surg. Path., 2001, 25, 1397.

Luo, J et. al., Cancer. Res., 2002, 62, 2220.

Reis-Filho et al, Virchows Arch. (2003) vol. 443, pp. 122-132.

12 pages from catalog: "product information form the Sigma-Aldrich Online Catalog" at sigmaaldrich.com/ . . . /ProductDetail.do?I . . . accessed Feb. 14, 2011.

8 pages from catalog: "product information form the Sigma-Aldrich Online Catalog" at sigmaaldrich.com/ . . . /ProductDetail.do?I . . . accessed Feb. 16, 2011.

Epstein, JI, and Netto, GJ., Biopsy interpretation of the prostate, 2008, Lippincott, Williams & Wilkins: Philadelphia, p. 99.

BioSB p40 IHC of p40 on an FFPE Prostate Tissue, http://www.biosb.com/p40-page, Jul. 29, 2015, 4 pages.

Reid-Nicholson M. et al. Immunophenotypic diversity of endometrial adenocarcinomas: implications for differential diagnosis. Mod Pathol. Aug. 2006; 19(8)1091-100.

Zhang P. et al. Immunohistochemical analysis of thyroid-specific transcription factors in thyroid tumors. Pathol Int 2006;56:240-245.

Ozcan A. et al. PAX 8 expression in non-neoplastic tissues, primary tumors, and metastatic tumors: a comprehensive inimunohistochernical study. Mod Pathol 2011;24:751-764.

Laury A.R. et al. A comprehensive analysis of PAX8 expression in human epithelial tumors. Am J Surg Pathol 2011;35:816-826.

Moretti L. et al. N-terminal PAX8 polyclonal antibody shows cross-reactivity with N-terminal region of PAX5 and is responsible for reports of PAX8 positivity in malignant lymphomas. Mod Pathol 2011.

Long K. B. et al. PAX8 Expression in well-differentiated pancreatic endocrine tumors: correlation with clinicopathologic features and comparison with gastrointestinal and pulmonary carcinoid tumors. Am J Surg Pathol 2010;34:723-729.

Haynes C. M. et al. PAX8 is expressed in pancreatic well-differentiated neuroendocrine tumors and in extrapancreatic poorly differentiated neuroendocrine carcinomas in fine-needle aspiration biopsy specimens. Cancer Cytopathol 2011;119:193-201.

Sangoi A. R. et al. PAX8 expression reliably distinguishes pancreatic well-differentiated neuroendocrine tumors from ileal and pulmonary well-differentiated neuroendocrine tumors and pancreatic acinar cell carcinoma. Mod Pathol 2011;24:412-424.

Lorenzo P.I. et al. Immunohistochemical assessment of Pax8 expression during pancreatic islet development and in human neuroendocrine tumors. Histochem Cell Biol 2011;136:595-607.

(56) References Cited

OTHER PUBLICATIONS

Ye J. et al. Diagnostic utility of PAX8, TTF-1 and napsin A for discriminating metastatic carcinoma from primary adenocarcinoma of the lung. Biotech Histochem 2011.
Albadine R. et al. PAX8 (+)/p63 (-) immunostaining pattern in renal collecting duct carcinoma (CDC): a useful immunoprofile in the differential diagnosis of CDC versus urothelial carcinoma of upper urinary tract. Am J Surg Pathol 2010;34:965-969.
Laury A.R. et al. PAX8 reliably distinguishes ovarian serous tumors from malignant mesothelioma. Am J Surg Pathol 2010;34:627-635.
Turque N. et al. Pax-QNR/Pax-6, a paired box- and homeobox-containing gene expressed in neurons, is also expressed in pancreatic endocrine cells. Mol Endocrinol 1994;8:929-938.
Tockman et al, Consideration in Bringing a Cancer Biomarker to Clinical Application. Cancer Research vol. 52 p. 2711s (1992).
Janicke et al., Urokinase-type Plasminogen Activator (u-PA) Antigen in a Predictor of Early Relapse in Breast Cancer. Fibrinolysis vol. 4 p. 69 (1990).
Paul, Structure and Function of Immunoglobulins. Fundemental Immunology, 3rd Edition, 1993, pp. 292-295.
Rudikoff et al Single Amino Acid Substitution Altering Antigen-binding Specificity (Proc. Natl. Acad. Sci. USA 1982 vol. 79: p. 1979-82).
De Pascalis et al., Grafting of "Abbreviated" Complementarity-Determining Regions Containing Specificity-Determining Residues Essential for Ligand Contact to Engineer a Less Immunogenic Humanized Monoclonal Anitbody. (The Journal of Immunology (2002) 169,3076-3084).
Brown et al. Tolerance to Single, but Not Multiple, Amino Acid Replacements in Anitbody VH CDR2. (J. Immunol. May 1996; 156(9):3285-3291.
Casset et al. A Peptide Mimetic of an Anti-CD4 Monoclonal Antibody by Rational Design. (2003) BBRC 307, 198-205.
Brown, H. M. et al. Uroplakin-III to Distinguish Primary Vulvar Paget Disease From Paget Disease Secondary to Urothelial Carcinoma, Human Path. 2002;33:545-548.
Koga, F. et al. Impaired p63 Expression Associates with Poor Prognosis and Uroplakin III Expression in Invasive Urothelial Carcinoma of the Bladder, Clin Cancer Res. 2003;9:5501-5507.
Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003;27:1434-1441.
Matsumoto, K. et al. Loss Expression of Uroplakin III is Associated with Clinicopathologic Features of Aggressive Bladder Cancer, Urology. 2008;72:444-449.
Mhawech, P. et al. Immunohistochemical Profile of High-Grade Urothelial Bladder Carcinoma and Prostate Adenocarcinoma, Human Path. 2002;33:1136-1140.
Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract. Am J Pathol. 1999;155:1047-1050.
Ohtsuka, Y. et al. Loss of uroplakin III expression is associated with a poor prognosis in patients with urothelial carcinoma of the upper urinary tract, BJU International, 2006;97:1322-1326.
Parker, D. C. et. al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003;27:1-10.
Wu, X. R. et. al. Mammalian Uroplakins, a group of highly conserved urothelial differentiation-related membrane proteins, J Biol Chem. 1994;269:13716-13724.
Moll, R. et al. Uroplakins, Specific Membrane Proteins of Urothelial Umbrella Cells, as Histological Markers of Metastatic Transitional Call Carcinomas. Am J Pathol, vol. 147, No. 5, Nov. 1995.
Kaufmann, O. et al. Uroplakin III Is a Highly Specific and Moderately Sensitive Immunohistochemical Marker for Primary and Metastatic Urothelial Carcinomas, Am J Clin Pathol 2000;113:683-687.
Wu XR, Kong XP, Pellicer A, Kreibich G, Sun TT.; Uroplakins in urothelial biology, function, and disease; Kidney Int. Jun. 2009;75(11):1153-65.
Wu X, Kakehi Y, Zeng Y, Taoka R, Tsunemori H, Inui M. J ; Uroplakin II as a promising marker for molecular diagnosis of nodal metastases from bladder cancer: comparison with cytokeratin 20.; Urol. Dec. 2005;174(6):2138-4.
Olsburgh J, Harnden P, Weeks R, Smith B, Joyce A, Hall G, Poulsom R, Selby P, Southgate J.J; Uroplakin gene expression in normal human tissues and locally advanced bladder cancer Pathol. Jan. 2003;199(1):41-9.
Lu JJ, Kakehi Y, Takahashi T, Wu XX, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. Aug. 2000;6(8):3166-71.
Li, S.M., et al. Detection of circulating uroplakin-positive cells in patients with transitional cell carcinoma of the bladder; .J Urol. Sep. 1999;162(3 Pt 1):931-5.
Kong XT, Deng FM, Hu P, Liang FX, Zhou G, Auerbach AB, Genieser N, Nelson PK, Robbins ES, Shapiro E, Kachar B, Sun TT.; Roles of uroplakins in plaque formation, umbrella cell enlargement, and urinary tract diseases. J Cell Biol. Dec. 20, 2004;167(6):1195-204.
Okegawa T, Kinjo M, Nutahara K, Higashihara E.; Value of reverse transcription polymerase chain assay in peripheral blood of patients with urothelial cancer. J Urol. Apr. 2004;171(4):1461-6.
Hong-Ying Huang, Shahrokh F. Shariat, Tung-Tien Sun, Herbert Lepor, Ellen Shapiro, Jer-Tsong Hsieh, Raheela Ashfaq, Yair Lotan, and Xue-Ru Wu, ; Persistent Uroplakin Expression in Advanced Urothelial Carcinomas: Implications in Urothelial Tumor Progression and Clinical Outcome. Hum Pathol. Nov. 2007; 38(11): 1703-1713.
Lai, Y. et al. UPK3A: A promising novel urinary marker for the detection of bladder cancer, Urology 76(2), 2010.
Saeb, Parsy, et al. 'Diagnosis of Bladder Cancer by Immunocytochemical detection of minichromosome maintenance protein-2 in cells retrieved from urine' British Journal of Cancer (2012) 107, 1384-1391.
Panka et al. Variable region framework differences result in decreased or increased affinity of variant anti-digoxin antibodies. Proc. Natl. Acad. Sci. USA, vol. 85, pp. 3080-3084, May 1988.
Harris et al. Assessing Genetic Heterogeneity in Production Cell Lines: Detection by Peptide Mapping of a Low Tyr to Gln Sequence Variant in a Recombinant Antibody. Biotechnology, vol. 11 p. 1293-1297, Nov. 1993.
Sanderson, SO et. al., "An Analysis of the p63/α-Methylacyl Coenzyme A Racemase Immunohistochemical Cocktail Stain in Prostate Needs Biopsy Speciments and Tissue Microarrays", Am. J. Olin. Path., 2004; 121:220-225.
Okazaki et al. Hydronephrosis associated with antiurothelial and antinuclear autoantibodies in Balb/ c-Fcgr2b-/- Pdcd1-/- mice. The Journal of Experimental Medicine. vol. 202, No. 12, pp. 1643-1648, Dec. 19, 2005.
Bondurand, et al. The role of SOX10 during enteric nervous system development. Dev Biol. Epub May 2, 2013, 382(1):330-43.
GenBank Accession No. CAG30470. SOX10 (*Homo sapiens*]. Oct. 16, 2008. (Retrieved from the Internet Dec. 4, 2014: <http://www.ncbi.nlm.nih.gov/protein/CAG30470.1>] 2 pages.
International Application No. PCT/US13/76203, entitled Antibody Cocktail Systems and Methods for Classification of Histological Subtypes in Lung Cancer, filed Dec. 18, 2013, Search Report, dated Jul. 8, 2014. 6 pages.
International Application No. PCT/US13/76203, entitled Antibody Cocktail Systems and Methods for Classification of Histological Subtypes in Lung Cancer, filed Dec. 18, 2013, Written Opinion, dated Jul. 8, 2014. 10 pages.
U.S. Appl. No. 61/738,938 entitiled "Systems and Methods for Antibody Cocktails for Classification of Histologic Subtypes in Lung Cancer" filed Dec. 18, 2012.
Tacha et al. 'A 6-Anitbody Panel for the Classification of Lung Adenocarcinoma Versus Squamous Cell Carcinoma.' Appl Immunohistochem Mol Morphol. 20(3): 201-7, May 2012.

(56) References Cited

OTHER PUBLICATIONS

Baty et al. 'Gene profiling of Icinical routine biopsies and prefiction of survival in non-small cell lung cancer.' Am J Respir Grit Care Med. 181(2):181-8.15 Oct. 2009.

Chopra, N. et al. 'Inducing Protectice Antibodies Against Ring-Infected Erythrocyte Surface Peptide Antigen of Plasmodium Falciparum Using Immunostimulating Complex (Iscoms) Delivery.' Med Microbiol. Immunol. Nov. 2000 vol. 189, No. 2: pp. 75-83.

Calbiochem-Novabiochem International. P40(Ab-1) Cat# PC373 [datasheet]. USA 2000; 2 pages.

Abcam. Understanding Secondary Antibodies: Fragment Antigen Binding Antibodies and Isotopes. USA 2012; 12 pages.

Biocare Medical. MACH 2 Double-Stain 2 [datasheet]. USA Mar. 2, 2011; 2 pages.

Yamaguchi, K. et al. Circulating Antibodies to P40AIS in the Sera of Respiratory Tract Cancer Patients. Int. J. Cancer. Nov. 20, 2000. vol. 89 No. 6; 5 pages.

Vaidyanathan, P. Aperio-Definins Digital Pathology Solutions [Presentation]. Jul. 7, 2011. Aperio Webinar. <http://www.aperio.com/sites/default/files/events/070611_Spectrum_Plus_ppt_for_webinar_on_integration.pd>; 10 pages.

Jain, et al. Atypical ductal hyperplasia: interobserver and intraobserver variability. Mod. Pathol. (2011) 24, 917-923.

Tacha, et al. "An Immunohitochemical Analysis of a Newly Developed Mouse Monocloncal p40 (BC28) in Lung, Bladder, Skin, Breast, Prostate, and Head and Neck Cancers" 2014 College of American Pathologists, Early Online Release, Arch Pathol. Lab Med. 8 pages, postes Feb. 2014.

Barbareschi, et al. p63, a p53 homologue, is a selective nuclear marker of myoepithelial cells of the human breast. Am J Surg. Pathol 25(8): 1054-1060,Aug. 2001.

Bergholz, et al. 'Role of p63 in development, tumorigenesis and cancer progression'. Cancer Microenvironment (2012) 5:311-322.

Di Como, et al. 'p63 Expression Profiles in Human Normal and Tumor Tissues'. Clinical Cancer Research. vol. 8, 494-501, Feb. 2002.

Hibi, et al. 'AIS is an oncogene amplified in squamous cell carcinoma'. Pro Natl Acad Sci U.S.A, May 9, 2000, vol. 97, No. 10, 5462-5467.

Kaghdad, et al. Monoallelically Expressed Gene Related to p53 a 1p36, a Region Frequently Deleted in Neuroblastoma and Other Human Cancers. Cell, vol. 90(4), 809-819, Aug. 22, 1997.

Karni-Schmidt, et al. Distinct Expression Profiles of p63 Variants during Urothelial Development and Bladder Cancer Progression. Am J Pathol vol. 178, No. 3, Mar. 2011, 1350-60.

Khoury, et al. "p53 Isoforms: An Intracellular Microprocessor?" Genes & Cancer, 2(4), 2011, 453-465.

Murray-Zmijewski, et al. p53/p63/p73 isoforms: an orchestra of isoforms to harmonise cell differentiation and response to stress. Cell Death and Differentiation (Jun. 2006); 13(6), 962-972.

Nobre, et al. 'p40: a p63 isoform useful for lung cancer diagnosis—a Review of the Physiological and Pathological Role of p63'. Acta Cytologica 2012; 57(1):1-8.

Nonaka, 'A study of Np63 expression in lung non-small cell carcinomas'. Am J Surg Pathol vol. 36 No. 6 Jun. 2012 895-9.

Nylander, et al. 'Differential expression of p63 isoforms in normal tissues and neoplastic cells'. J Pathol 2002; 198: 417-427.

Osada, et al. Cloning and functional analysis of human p51, which structurally and functinoally resembles p53, Nat Med. Jul. 1998; 4(7): 839-43.

Pelosi, et al. 'Np63 (p40) and Thyroid Transcription Factor-1 Immunoreactivity on small biopsies or cellblocks for typing non-small cell lung cancer'. Journal and Thoracic Oncology, vol. 7(2), No. 2, Feb. 2012, 281-90.

Senoo et al. 'A second p53-Related Protein, p73L, with High Homology to p73'. Biophys Res Commun. Jul. 30, 1998; 248(3), 603-607.

Trink, et al. A new human p53 homologue, Nat Med. Jul. 1998; 4(7): 747-8.

Yang, et al. 'p63, a p53 homolog at 307-29, encodes multiple products with transactivating, death-inducing, and dominant-negative activities'. Molecular Cell, vol. 2(3), 305-316, Sep. 1998.

Bowen, et al. 'Emerging roles for PAX8 in ovarian cancer and endosalpingeal development.' Gynecologic Oncology, vol. 104, No. 2, Feb. 2007, 331-337.

Tacha, D. et al. Expression of PAX8 in Normal and Neoplastic Tissues: A Comprehensive Immunohistochemical Study. Appl. Immun. Mol. Morph. 2011.

Kobel M. et al. Ovarian carcinoma subtypes are different diseases: Implications for biomarker studies. PLoS Med. Dec. 2, 2008; 5(12): e232.

Nonaka D. et al. Expression of PAX8 as useful marker in distinguishing ovarian carcinomas from mammary carcinomas. Am J Surg Pathol. Oct. 2008; 32(10):1566-71.

Tong G. X. et al. Expression of PAX8 in nephrogenic adenoma and clear cell adenocarcinoma of the lower urinary tract: evidence of related histogenesis? Am J Surg Pathol. Sep. 2008; 32(9):1380-7.

Tong G. X. et al. Expression of PAX8 in normal and neoplastic renal tissues: an immunohistochemical study. Mod. Pathol. Sep. 2009; 22 (9):1218-27.

Mazal P. R. et al. Expression of aquaporins and PAX-2 compared to CD10 and cytokeratin 7 in renal neoplasms: a tissue rnicroarray study. Mod. Pathol. Apr. 2005; 18(4):535-40.

Avery A. K. et al. Use of antibodies to RCC and CD10 in the differential diagnosis of renal neoplasms. Am J Surg Pathol. Feb. 2000; 24(2):203-10.

Zhou M. et al. The usefulness of immunohistochemical markers in the differential diagnosis of renal neoplasms. Clin Lab Med. Jun. 2005; 25(2):247-257.

Kuehn A. et al. Expression analysis of kidney-specific cadherin in a wide spectrum of traditional and newly recognized renal epithelial neoplasms: diagnostic and histogenetic implications. Am J Surg Pathol. Oct. 2007; 31(10):1528-33.

Mazal P. R. et al. Expression of kidney-specific cadherin distinguishes chromophobe renal cell carcinoma from renal oncocytoma. Hum Pathol. Jan. 2005; 36(1):22-8.

Zhu W. et al. WT1, monoclonal CEA, TTF1, and CA125 antibodies in the differential diagnosis of lung, breast, and ovarian adenocarcinomas in serous effusions. Diag Cytopathol. Jun. 2007; 35(6):370-5.

Tomos C. et al. Expression of WT1, CA 125, and GCDFP-15 as useful markers in the differential diagnosis of primary ovarian carcinomas versus metastatic breast cancer to the ovary. Am J Surg Pathol. Nov. 2005; 29(11):1482-9.

Lee A. H. et al. The expression of Wilms' tumour-1 and CA125 in invasive micropapillary carcinoma of the breast. Histopathology. Dec. 2007; 51(6):824-8.

Kreitzer et al., "A robust method to derive functional neural crest cells from human pluripotent stem cells" Am J Stem Cell 2013;2(2):119-131.

Kang, et al., "Diagnostic Utility of SOX10 to distinguish malignant peripheral nerve sheath tumor from synovial sarcoma, including intraneural synocial sarcoma" Modem Pathology (2014) 24, 55-61.

Santa Cruz Biotechnology, Inc. "Sox-10 (N-20): sc-17342" date of publication unknown. 1 page.

Abcam "Anti-SOX10 antibody ab108408" date of publication unknown. 4 pages.

Aung, et al. "KBA62 and PNL2: Two Newer Melanoma Markers—Immunohisto-Chemical Analysis of 1563 Tumors including Metastatic, Desmoplastic, and Musocal Melanomas and their Mimics" Am J Surg Pathol Feb. 2012 ; 36 (2):265-272.

"p40 (5-17) Antibody from" © 1980-2013 Linscott's Directory. 3 pages. Date retrieved: Sep. 27, 2016.

Creative Biolabs, Chimeric IgG construction; (c) 2007-2016 Creative Biolabs, 2 pages.

U.S. Appl. No. 15/811,458, filed Nov. 13, 2017. First Named Inventor: Tacha.

Wu, et al. Uroplakin II Gene Is Expressed in Transitional Cell Carcinoma But Not in Bilharzial Bladder Squamous Cell Carcinoma: Alternative Pathways of Bladder Epithelial Differentiation and Tumor Formation. Cancer Research 28, 1291-1297, Mar. 15, 1998.

(56) References Cited

OTHER PUBLICATIONS

Japanese Patent Application No. 2015-534675. English Translation of the Rejection dated Aug. 2, 2017. 6 pages.
European Patent Application No. 13841542.7, Notice of Intended Grant of Patent dated Jan. 3, 2018. 8 pages.
Kim J-K et al: Localization of the site of the murine IGG1 Molecule that is involved in binding to the murine intestinal FC Receptor European Journal of Immunology, vol. 24, No. 10, Jan. 1, 1994, pp. 2429-2434.
Pelosi et al (Journal of Thoracic Oncology, 2011, 6(6)(sup 2): S335-S336) 7 pages.
Nagashio et al., Detection of tumor-specific autoantibodies in sera of patients with lung cancer (Lung Cancer, 2008, 62: 364-373).
Rekhtman et al., (Modem Pathology, 2011, 24: 1348-1359).
European Application No. 14850426.9, European Search Report dated Mar. 9, 2017. 11 pages.
Ohtomo et al., SOX10 is a novel marker of acinus and intercalated duct differentiation in salivary gland tumors: a clue to this histogenesis for tumor diagnosis. Modern Pathology, 26 [Epub Apr. 2013], 1041-1050.
Tomoo Koh, Immunohistochemistry in Diagnostic Surgical Pathology, Microscope, vol. 48, No. 1 (Apr. 2013), p. 33-38.
Multiplex IHC Antibody Cocktail, Funakoshi Co., Ltd., Aug. 30, 2012, [Retrieved on Aug. 24, 2018] web page #: 4567, Retrieved from the Internet, URL: https://www.funakoshi.co.jp/contents/4567. 5. pages.
Japanese Patent Application No. 2016-519763, English Translation of the Office Action dated Aug. 27, 2018. 10 pages.
Bradbury Andrew R M et al: When monoclonal antibodies are not monospecific: Hybridomas frequently express additional functional variable regions., MABS, vol. 10, No. 4, May 2018 (May 2018) pp. 539-546 ISSN:1942-0870.
Vilches-Moure, Jose et al., Comparison of Rabbit Monoclonal Antibodies in Immunohistochemistry in Canine Tissues. J Vet Diang Invest 17:346-350 (2005).
European Patent Application No. 14850426.9, Office Action dated Oct. 11, 2018. 11 pages. Received Oct. 18, 2018.
U.S. Appl. No. 15/811,458, filed Nov. 13, 2017. First Named Inventor: Tacha. Notice of Allowance dated Oct. 18, 2018. 9 pages.
U.S. Appl. No. 15/811,458, filed Nov. 13, 2017. First Named Inventor: Tacha. Notice of Allowance dated Feb. 6, 2019. 5 pages.
U.S. Appl. No. 13/830,473 filed Mar. 14, 2013. First Named Inventor: Qi. Notice of Allowance dated Oct. 12, 2018. 7 pages.
U.S. Appl. No. 13/830,473 filed Mar. 14, 2013. First Named Inventor: Qi. Notice of Allowance dated Mar. 11, 2019. 9 pages.
European Patent Application No. 14756627.7. Decision to Grant a European Patent, dated Mar. 7, 2019. 2 pages.
Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162.
Brown, et al."Tissue-Preserving Antibody Cocktails to Differentiate Primary Squamous Cell Carcinoma, Adenocarcinoma, and Small Cell Carcinoma of Lung", Arch Pathol Lab Med vol. 137, Sep. 2013.
Savci-Heijink C. D., et al. The role of desmoglein-3 in the diagnosis of squamous cell carcinoma of the lung. Am J Pathol. 2009;174(5): 1629-1637.
Ring B. Z., et al. A novel five-antibody immunohisto- chemical test for subclassification of lung carcinoma. Mod Pathol. 2009;22(8): 1032-1043.
Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 5/6. Am J Surg Pathol, 2011; 35(1): 15-25.
Bishop J. A., p40 (ΔNp63) is superior to p63 for the diagnosis of pulmonary squamous cell carcinoma, Modern Pathology (2011), 1-11; republished Mar. 2012;25(3):405-15.
Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. Feb. 2, 2006;6:31.

* cited by examiner

US 10,429,390 B2

ANTIBODY COCKTAIL SYSTEMS AND METHODS FOR CLASSIFICATION OF HISTOLOGIC SUBTYPES IN LUNG CANCER

PRIORITY CLAIM

This application is the United States National Phase of International Patent Application Number PCT/US2013/076203 filed 18 Dec. 2013 which claims priority to and the benefit of U.S. Provisional Application No. 61/738,938 filed Dec. 18, 2012, each application hereby incorporated by reference herein in its entirety.

TECHNICAL FIELD

This invention relates to the field of lung cancer and compositions for improved detection of lung cancer, non-small cell lung carcinoma (NSCLC), adenocarcinoma (ADC), squamous cell carcinoma (SCC), methods and uses thereof to detect lung cancer as well as its diagnostic and/or prognostic uses.

BACKGROUND OF THE INVENTION

Microscopic examination of tissue samples, particularly those obtained by biopsy, is a common method for diagnosis of disease. In particular, immunohistochemistry (IHC), a technique in which specific antibodies are used to detect expression of specific proteins in the tissue sample, is a valuable tool for diagnosis, particularly for the detection and diagnosis of cancer.

Lung cancer is the leading cause of cancer death for both men and women. More people die of lung cancer than of colon, breast, and prostate cancers combined. Non-small cell lung carcinoma (NSCLC) comprises approximately 80% of lung cancers and may be classified into several histological types, most commonly include adenocarcinoma (ADC) or even squamous cell carcinoma (SCC). Classification of lung carcinomas into histological types may be performed by morphological examination using hematoxylin and eosin (H&E) or immunohistochemistry, and in some cases even, mucin stains; however, accurate classification can be difficult with poorly differentiated or even undifferentiated lung carcinoma. Diagnosis can be further complicated by the use of needle core biopsies, which provide limited amounts of tissue for both immunohistochemistry and molecular testing, and may include crush artifacts. Additionally, cytology specimens may lack morphological features necessary for diagnosis with H&E alone.

Although the majority of lung cancers (particularly grades I and II) can be diagnosed with only H&E staining, with the advent of targeted therapies, diagnostic needs have changed, and an improved method for classification of a greater number of NSCLC cases is needed. In the past, histologic subtyping of NSCLCs had limited diagnostic value, due to the fact that the same treatment may have been provided to the patient, perhaps regardless of NSCLC subtype. However, the availability of targeted therapies has created a need for accurate subtyping of NSCLC. For example, bevacizumab, a therapeutic humanized monoclonal antibody targeting vascular endothelial growth factor, may be a common treatment for NSCLC patients; however, patients with the SCC subtype should not receive bevacizumab, perhaps due to the about 30% mortality rate by fatal pulmonary hemorrhage. Furthermore, enhanced efficacy may have been demonstrated with the addition of premextred to conventional chemotherapy in non-squamous cell carcinomas, but may not in SCC. Therefore, accurate methods for subtyping NSCLC specimens may be useful for the best patient care, with optimal therapeutic efficacy and minimal adverse effects.

Immunohistochemistry may be commonly used to assist pathologists in determining histologic subtype of NSCLC specimens, perhaps particularly discriminating ADC from SCC, as well as from Small Cell Carcinomas of the lung. Historically, the antibodies TTF-1 and p63 may have been used in IHC to differentiate primary adenocarcinoma from squamous cell carcinoma of the lung. Both of these antibodies may suffer from limitations in sensitivity (e.g. TTF-1 may stain only about 70% of ADC cases) or specificity (p63, a marker for SCC, may stain about 11% of ADC cases). In order to improve sensitivity and specificity, antibody combinations may have been suggested for use in a panel that may improve diagnostic accuracy for histologic subtyping, perhaps over use of a single antibody. For example, in one study, a panel of TTF-1, p63, Napsin A and even CK5/6 was used to classify about 77% of poorly differentiated cases of NSCLC; however about 23% of the cases remained unclassified. Similarly, a five antibody panel that may include CK5/6, TRIM29, LAT-1, CEACAM5 and even MUC1 perhaps may be used in a weighted mathematical formula to classify about 85% of LADC cases and about 88% of lung SCC cases, respectively, perhaps while leaving about 12.8% of the cases unclassified. IHC with Napsin A and p63 may have also been suggested as a method to discriminate ADC from SCC. Each of these antibody panels may face certain limitations or deficiencies. For example, in each of these methods, multiple sections of a specimen may need to be stained, in order to obtain the diagnosis; this may be undesirable because limited tissue may be available and it may need to be conserved for other testing. Additionally, each of these methods may be unable to provide a diagnosis for all cases, leaving some specimens unclassified (e.g. limited sensitivity or the like), or they may inaccurately identify a histologic subtype (e.g. limited specificity or the like).

In one example, a series of cocktails containing two or more (e.g., at least two) primary antibodies may have been used in a two-color staining IHC procedure (also known as a "double-stain" or "Multiplex") perhaps to classify specimens as ADC or SCC in a more efficient manner and may even use fewer sections of the tissue specimen. When used in a diagnostic sequence, cocktails of Napsin A+Desmoglein-3, TTF-1+CK-5, and p63+TRIM-29, were about 94.7% sensitive and about 100% specific for ADC and SCC, in this study. With this method, about 7.1% of the specimens remained unclassified.

Several antibodies are known to be used independently, which may be useful in IHC methods and which may even provide increased sensitivity, specificity, and/or classification percentage, consume less of a specimen for testing, or even exhibit other advantages or the like.

Desmoglein 3 (DSG3 or DSG-3) may be a calcium-binding transmembrane glycoprotein component of desmosomes in vertebrate epithelial cells. As a result, IHC using a DSG3 antibody may produce membranous staining, perhaps not cytoplasmic. In one study, DSG3 was reported to stain about 98% of cases of SCC, while about 99% of non-SCC cases were negative.

Napsin A, a novel aspartic proteinase, may be normally expressed in type II pneumocytes, alveolar macrophages, renal tubules, exocrine glands, and even pancreatic ducts. Studies have shown that Napsin A may be a very specific marker for lung adenocarcinoma. The role of Napsin A in differentiating primary from metastatic ACA of the lung may have been reported. Although, it may occasionally stain non-pulmonary ACAs, Napsin A may be a useful marker in differentiating primary lung ACAs from SCCs. Positive immunohistochemical staining with Napsin A may show intense granular cytoplasmic reactivity.

Thyroid transcription factor-1 (TTF-1) may be a member of the NKX2 family of homeodomain transcription factors and may result in nuclear specific staining in IHC. It may be expressed in epithelial cells of the thyroid gland and even the lung. In one study, TTF-1 may have had a sensitivity of about 70% for cases of ADC, with a specificity of about 94.7% versus SCC (about 5.3% of SCC cases stained with TTF-1).

p63 may be a member of the p53 family of transcription factors. In normal tissues, IHC with p63 may be positive in squamous epithelia, in basal cells of urothelium and even in basal cells of prostate epithelium. IHC using a p63 antibody may result in nuclear staining. p63 may be detected in greater than about 80% of lung squamous cell carcinomas; however, greater than about 10% of lung adenocarcinomas may also stain for p63, which may be a limitation of specificity that may result in an equivocal or perhaps even an inaccurate diagnosis.

p40 is an isoform of the p63 gene family that may lack the N-terminal transactivation domain of p63. In IHC using a p40 antibody, one study found equal sensitivity for SCC when using p40 or p63; however, p40 may have exhibited superior specificity. In this study, p63 stained about 31% of lung ADC cases, but p40 stained only about 3% of these cases. IHC using a p40 antibody may result in nuclear staining. p40 and p63 may exhibit similar staining patterns and may be interchangeable for certain applications.

Cytokeratins (CK) may be the dominant, intermediate filament proteins of the epithelial cells. CK5 may be detected in normal cells, including: breast myoepithelial cells, prostate basal cells, and perhaps even the basal layer of the epidermis and even salivary glands. Positive immunohistochemical staining of CK5 may display a cytoplasmic staining pattern, which may be indicative of SCC. Positive immunohistochemical staining of CK7 may display a cytoplasmic staining pattern, which may be indicative of lung ADC.

Given the current state of the art, IHC methods with increased sensitivity and/or specificity in the classification of histologic subtypes of NSCLC specimens may be useful. Similarly, methods that have potential to classify a greater percentage of specimens (e.g., fewer specimens remain unclassified with the method), or even consume less of a specimen for testing, may also be useful. Additionally, methods that may improve agreement in classification between pathologists (e.g., concordance) may be valuable. Also, methods that may assist in determining the origin of a tumor, particularly as from the lung or an organ other than the lung, may be useful.

DISCLOSURE OF THE INVENTION

General embodiments of the present invention may include combinations of antibodies, methods for their preparation, and use in immunohistochemistry, or the like, for the diagnosis of cancer such as lung cancer or the like. In some embodiments, specific combinations of antibodies may be selected for use in distinguishing histologic subtypes of lung cancer such as but not limited to NSCLC.

The antibody combinations may be used in an immunohistochemistry procedure to simultaneously identify multiple antigens of diagnostic utility perhaps using one or more (e.g., at least one) chromogenic stains. In this manner, the antibodies may be known as "primary antibodies." The use of multiple primary antibodies in the IHC of a single specimen section may be known in the art; however, the particular primary antibody combinations most useful in lung cancer diagnosis, or identification of histologic subtypes, are not known and are needed.

Antibodies that bind human proteins can be obtained from a different species, such as mouse or rabbit, and may be used to identify their protein targets in human tissues by IHC. Many such antibodies may be commercially available, or may be prepared by methods well known in the art. IHC, or the like, can be performed on specimens from various sources, including formalin-fixed, paraffin-embedded tissue sections, frozen tissue sections, cytology specimens, pleural fluid, or the like. Generally, following incubation of one or more (e.g., at least one) primary antibodies with the specimen, a detection step may be performed, comprising incubation with one or more (e.g., at least one) antibody-enzyme conjugates, which may bind one or more (e.g., at least one) primary antibodies. In one or more (e.g., at least one) subsequent steps, one or more (e.g., at least one) chromogens may be applied, which may produce one or more (e.g., at least one) colored stains, which may even be localized near the microscopic location of the primary antibody, perhaps, potentially identifying the presence or absence, and/or location, of a primary antibody's target antigen in the specimen.

Some antibodies may be particularly useful in identifying a histologic subtype, such as squamous cell carcinoma, whereas, other antibodies may be useful in identifying a different histologic subtype, such as adenocarcinoma. In some cases, a double-stain (or Multiplex) IHC procedure may be performed using primary antibodies from two or more (e.g., at least two) host species (such as mouse or rabbit), perhaps in combination with two or more (e.g., at least two) antibody-enzyme conjugates, which may result in at least two colored stains that may be useful for identifying the presence or even absence of one or more (e.g., at least one) antibodies, perhaps even when two or more (e.g., at least two) chromogens are applied (such as DAB and Fast Red, when HRP and AP are used in the antibody-enzyme conjugates, respectively). Determining the presence or absence of particular proteins in a patient tissue sample, in this manner, may provide information to the pathologist or other clinician that may be useful in evaluating options for treatment of the patient, including, but not limited to the histologic subtype of the cancer.

Figure 30:
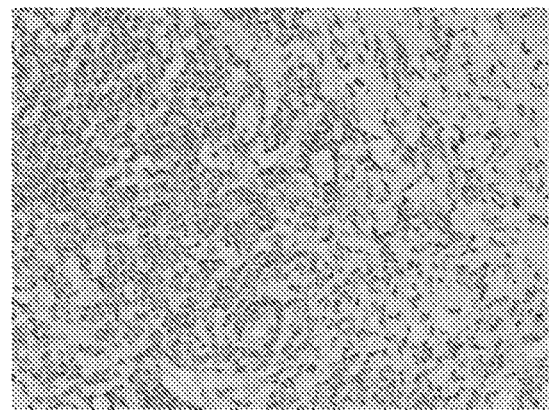

FIG. 30 shows an example of the antibody cocktail DSG-3+p40 staining a specimen of lung ADC. Staining of DSG-3 (brown, membranous) and p40 (red, nuclear) is reduced, or perhaps absent in this sample.

Figure 31:
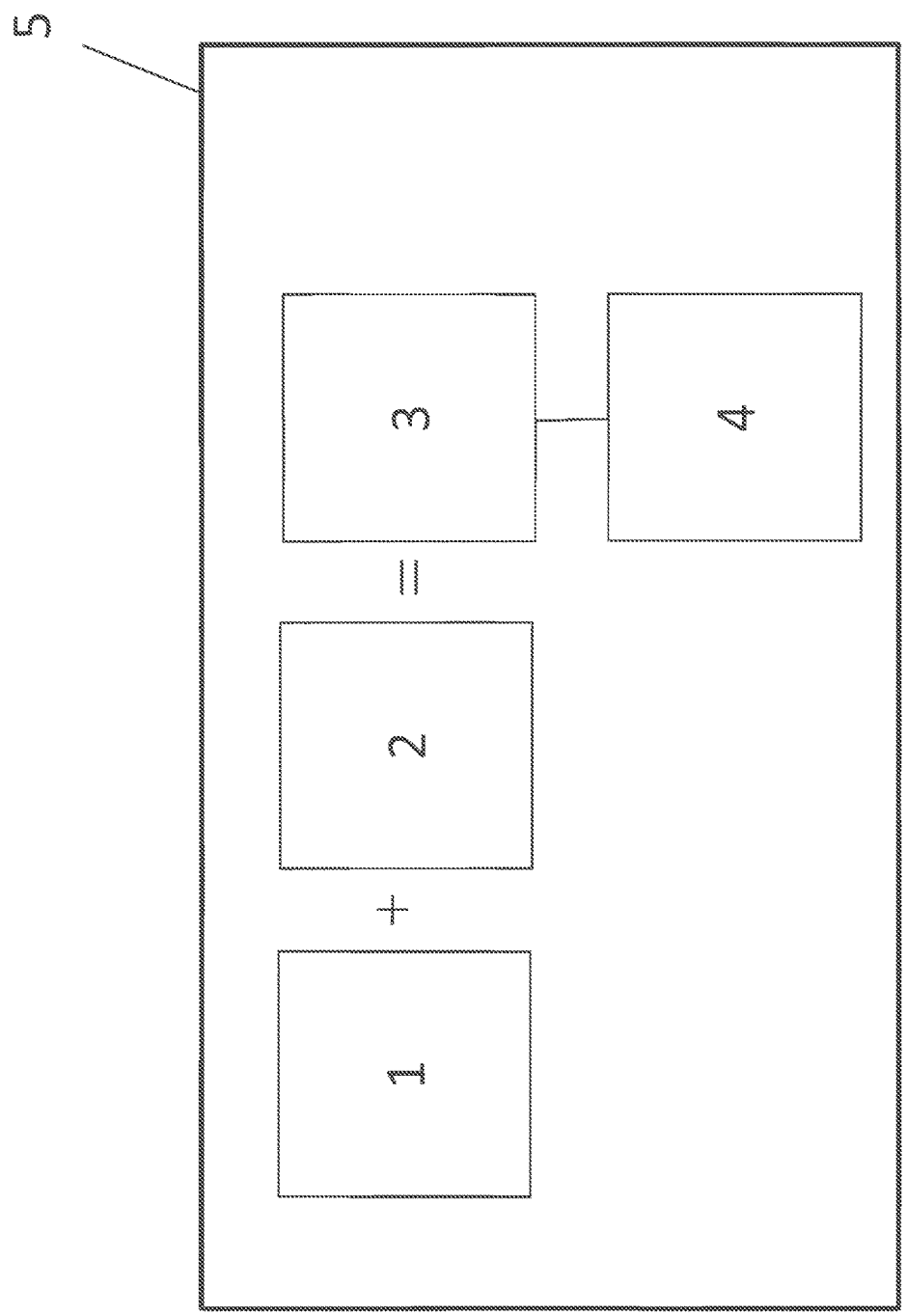

FIG. 31 shows an example of a schematic summary of a kit in accordance with various embodiments of the present invention.

Figure 32:
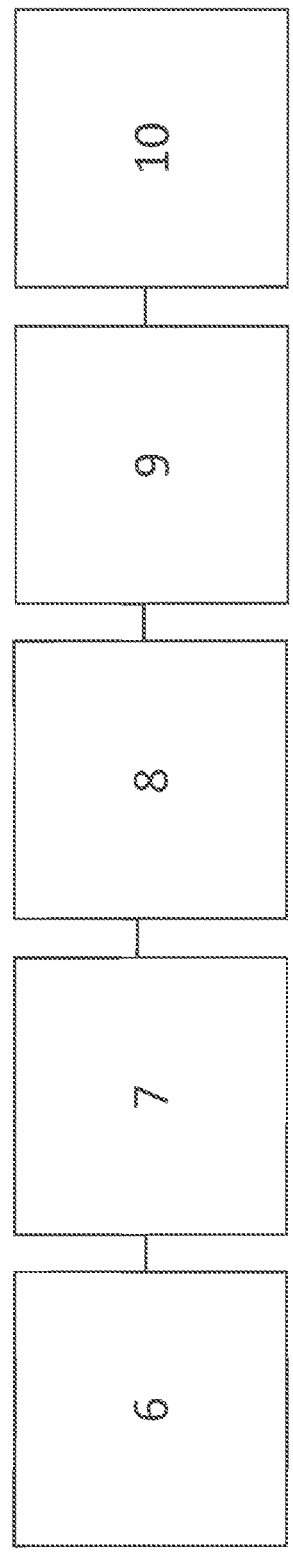

FIG. 32 shows an example of a schematic summary of a method in accordance with various embodiments of the present invention.

Figure 1:
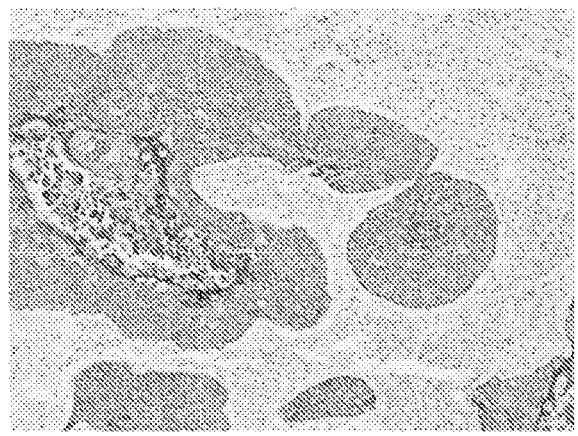
FIG. 1 shows an example of the antibody cocktail DSG-3+CK5/Napsin A staining a specimen of lung SCC. DSG-3 staining (brown) is membranous and CK5 staining (brown) is cytoplasmic. Napsin A staining (red, cytoplasmic) may be reduced, or perhaps absent in this sample.
Figure 33:
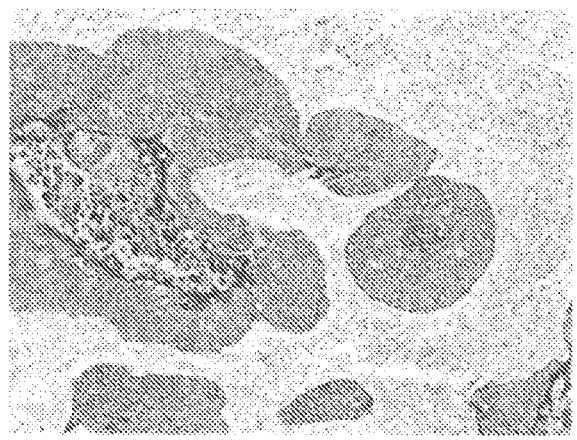

FIG. 33 shows a black and white version of the example of FIG. 1.

Figure 2:
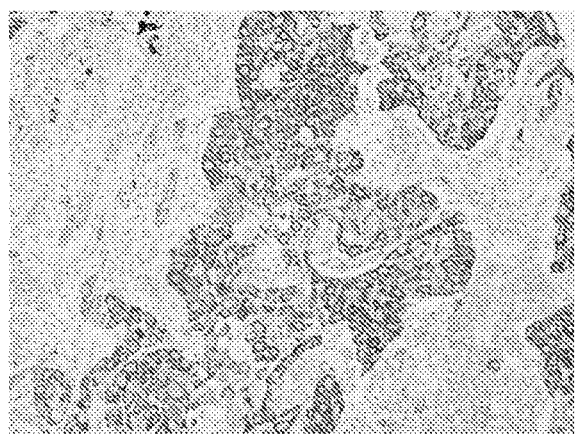
FIG. 2 shows an example of the antibody cocktail DSG-3+CK5/Napsin A staining a specimen of lung SCC, with some remaining normal lung, which may be Napsin A positive. DSG-3 staining (brown) is membranous and CK5 staining (brown) is cytoplasmic. Napsin A staining (red, cytoplasmic) may be reduced, or perhaps restricted to normal lung tissue, in this sample.
Figure 34:
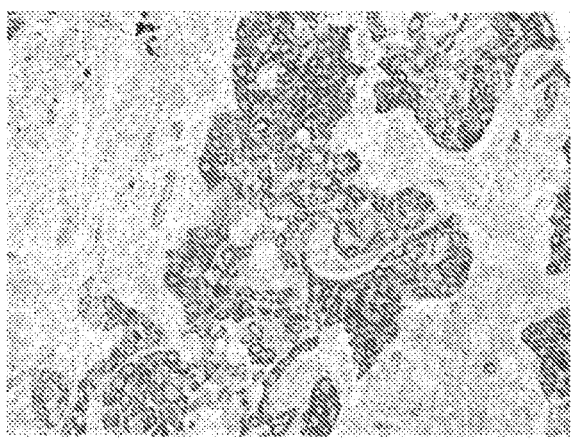

FIG. 34 shows a black and white version of the example of FIG. 2.

Figure 3:
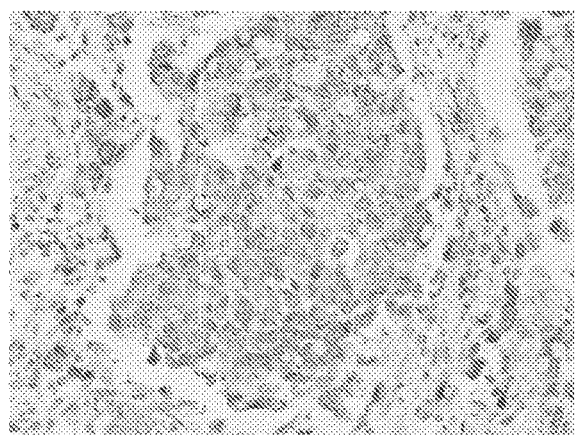
FIG. 3 shows an example of the antibody cocktail DSG-3+CK5/Napsin A staining a specimen of lung ADC, which may be poorly differentiated. Staining of Napsin A (red) is cytoplasmic. Staining of DSG-3 (brown, membranous) and CK5 (brown, cytoplasmic) may be reduced, or perhaps absent, in this sample.
Figure 35:
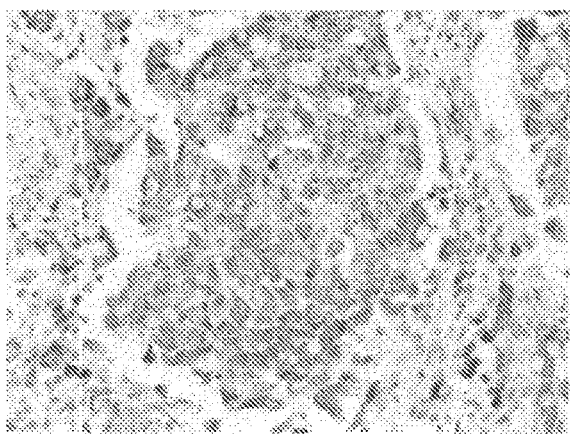

FIG. 35 shows a black and white version of the example of FIG. 3.

Figure 4:
FIG. 4 shows an example of the antibody cocktail DSG-3+CK5/Napsin A staining a specimen of lung ADC, which may be well differentiated. Staining of Napsin A (red) is cytoplasmic. Staining of DSG-3 (brown, membranous) and CK5 (brown, cytoplasmic) may be reduced, or perhaps absent, in this sample.
Figure 36:
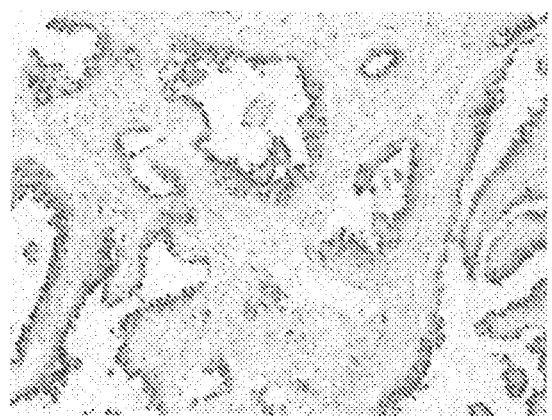

FIG. 36 shows a black and white version of the example of FIG. 4.

Figure 5:
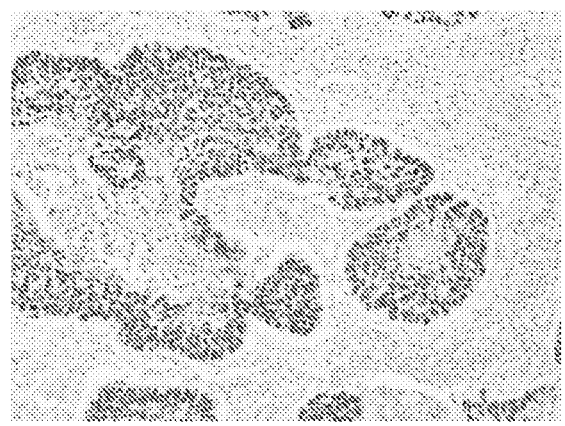
FIG. 5 shows an example of the antibody cocktail p40/TTF-1 staining a specimen of lung SCC. Staining of p40 (brown) is nuclear. Staining of TTF-1 (red, nuclear) may be reduced, or perhaps absent, in this sample.
Figure 37:
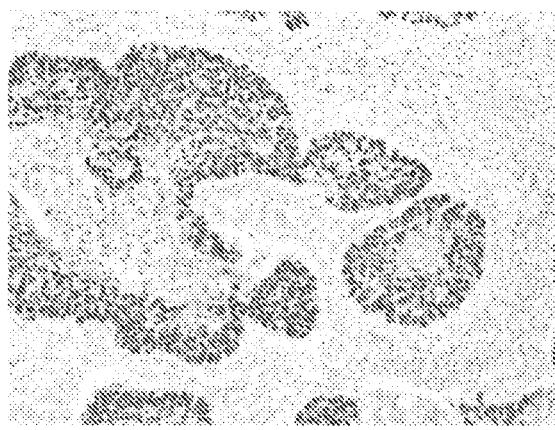

FIG. 37 shows a black and white version of the example of FIG. 5.

Figure 6:
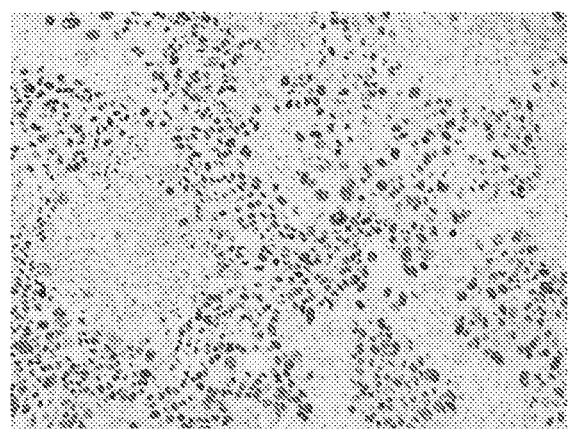
FIG. 6 shows an example of the antibody cocktail p40/TTF-1 staining a specimen of lung SCC. Staining of p40 (brown) is nuclear. Staining of TTF-1 (red, nuclear) may be reduced, or perhaps absent, in this sample.
Figure 38:
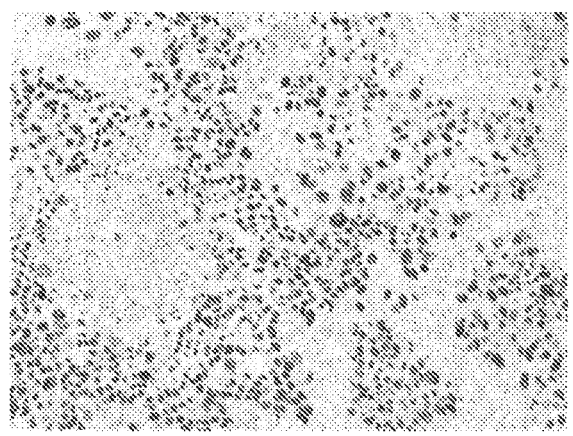

FIG. 38 shows a black and white version of the example of FIG. 6.

Figure 7:
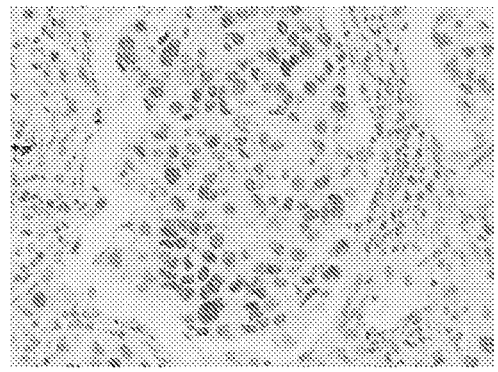
FIG. 7 shows an example of the antibody cocktail p40/TTF-1 staining a specimen of lung ADC, which may be poorly differentiated. Staining of TTF-1 (red) is nuclear. Staining of p40 (brown, nuclear) may be reduced, or perhaps absent, in this sample.
Figure 39:
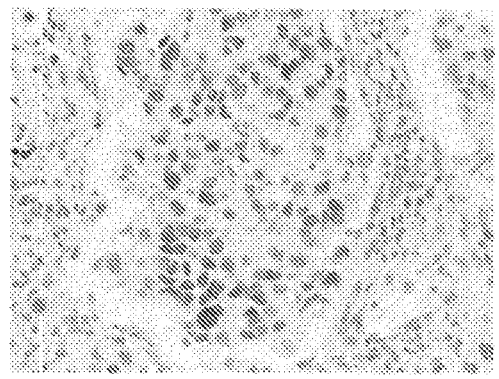

FIG. 39 shows a black and white version of the example of FIG. 7.

Figure 8:
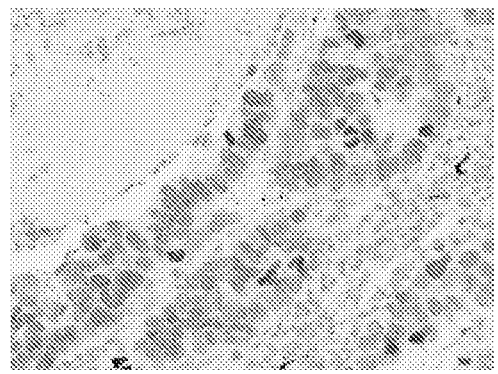
FIG. 8 shows an example of the antibody cocktail p40/TTF-1 staining a specimen of lung ADC, which may be moderately differentiated. Staining of TTF-1 (red) is nuclear. Staining of p40 (brown, nuclear) may be reduced, or perhaps absent, in this sample.
Figure 40:
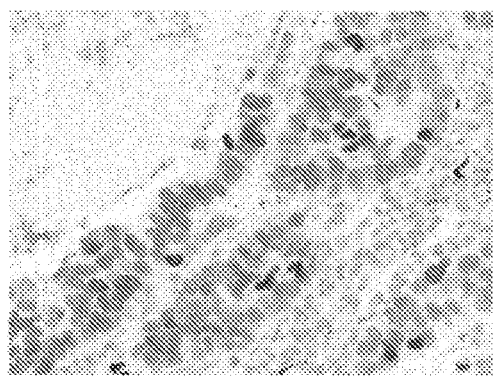

FIG. 40 shows a black and white version of the example of FIG. 8.

Figure 9:
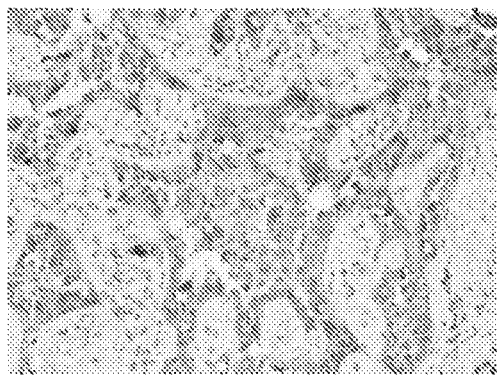
FIG. 9 shows an example of the antibody cocktail DSG-3+p40 (M)/Napsin A (RM) staining a specimen of lung ADC. Staining of Napsin A (red) is cytoplasmic. Staining of DSG-3 (brown, membranous) and p40 (brown, nuclear) may be reduced, or perhaps absent, in this sample.
Figure 41:
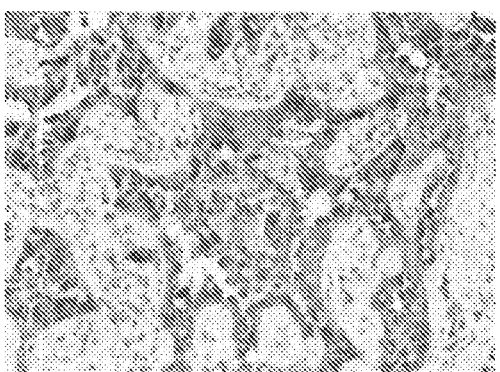

FIG. 41 shows a black and white version of the example of FIG. 9.

Figure 10:
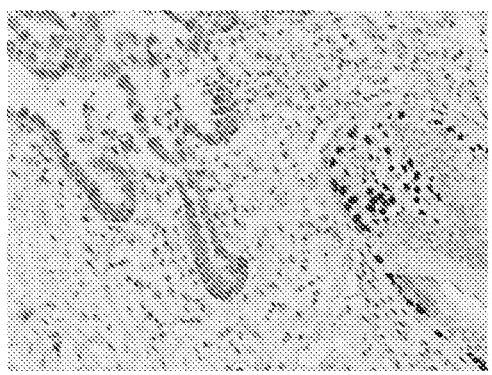
FIG. 10 shows an example of the antibody cocktail DSG-3+p40 (M)/Napsin A (RM) staining a specimen of lung ADC. Staining of Napsin A (red) is cytoplasmic. Staining of DSG-3 (brown, membranous) and p40 (brown, nuclear) may be reduced, or perhaps restricted to normal lung tissue, in this sample.
Figure 42:

FIG. 42 shows a black and white version of the example of FIG. 10.

Figure 11:
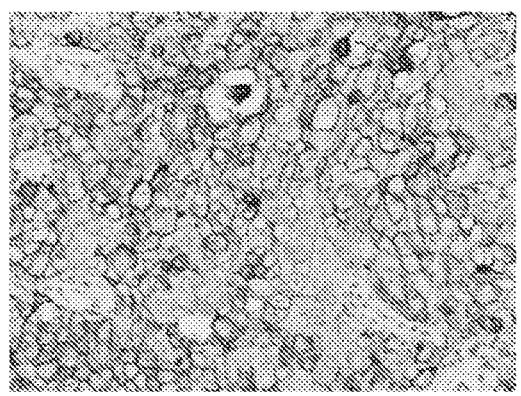
FIG. 11 shows an example of the antibody cocktail DSG-3+p40 (M)/Napsin A (RM) staining a specimen of lung SCC. Staining of DSG-3 (brown) is membranous. Staining of p40 (brown, nuclear) and Napsin A (red, cytoplasmic) may be reduced, or perhaps absent, in this sample.
Figure 43:
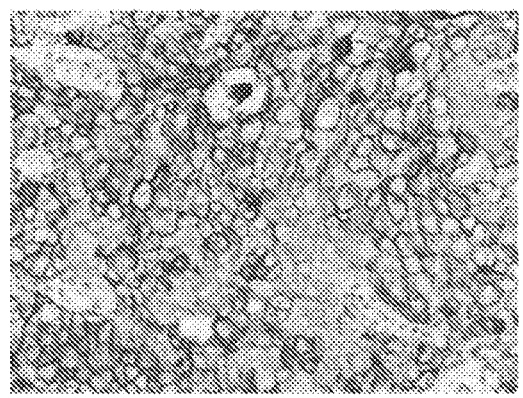

FIG. 43 shows a black and white version of the example of FIG. 11.

Figure 12:
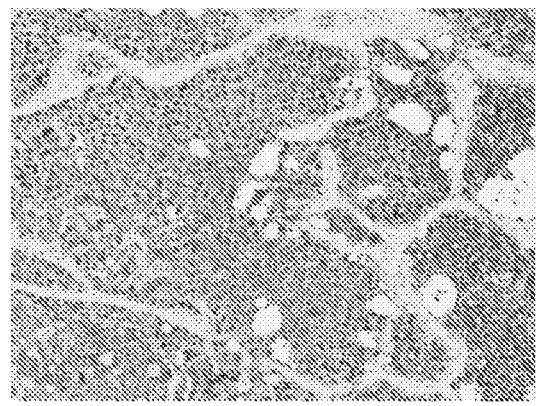
FIG. 12 shows an example of the antibody cocktail DSG-3+p40 (M)/Napsin A (RM) staining a specimen of lung SCC. Staining of DSG-3 (brown) is membranous and staining of p40 (brown) in nuclear. Napsin A (red, cytoplasmic) may be reduced, or perhaps restricted to normal lung tissue in this sample.
Figure 44:
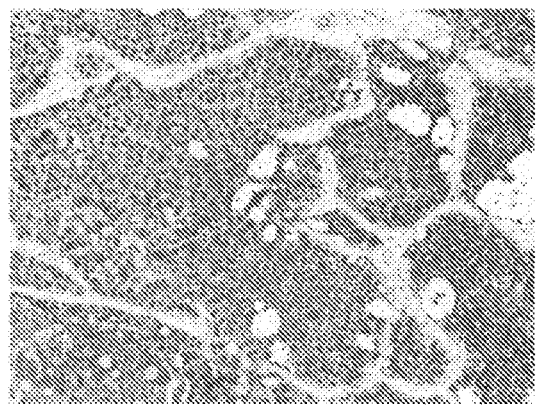

FIG. 44 shows a black and white version of the example of FIG. 12.

Figure 13:
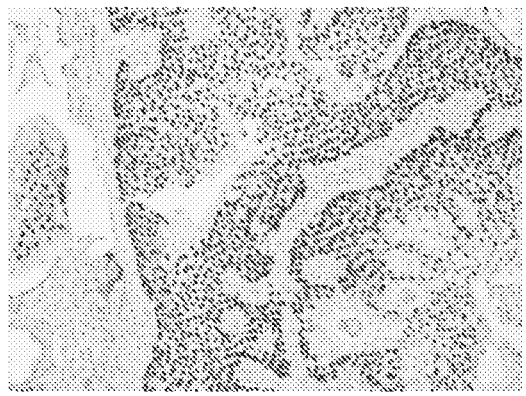
FIG. 13 shows an example of the antibody cocktail DSG-3+p40 (M)/Napsin A (RM) staining a specimen of lung SCC. Staining of p40 (brown) in nuclear. Staining of DSG-3 (brown, membranous) and/or Napsin A (red, cytoplasmic) may be reduced, or perhaps absent, in this sample.
Figure 45:
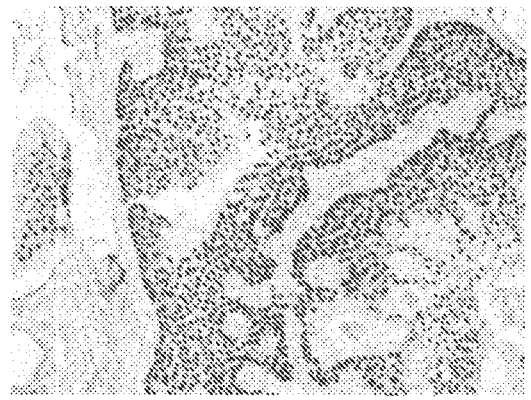

FIG. 45 shows a black and white version of the example of FIG. 13.

Figure 14:
FIG. 14 shows an example of the antibody cocktail DSG-3+p40 (M) staining a specimen of lung SCC. Staining of DSG-3 (brown) is membranous and staining of p40 (brown) in nuclear.
Figure 46:
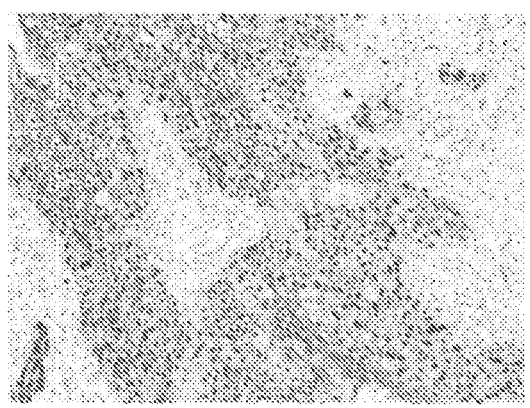

FIG. 46 shows a black and white version of the example of FIG. 14.

Figure 15:
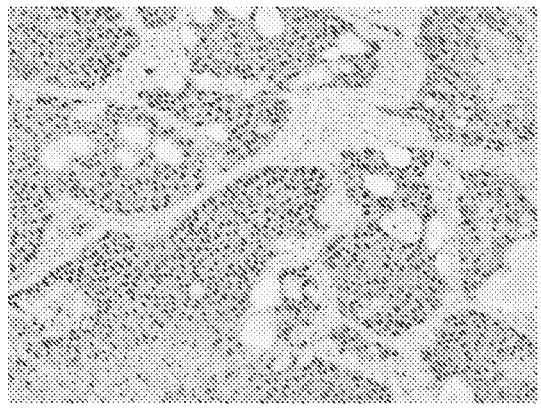
FIG. 15 shows an example of the antibody cocktail p40 (M)+CK5 (RM) staining a specimen of lung SCC. Staining of p40 (brown) is nuclear and staining of CK5 (red) is cytoplasmic.
Figure 47:
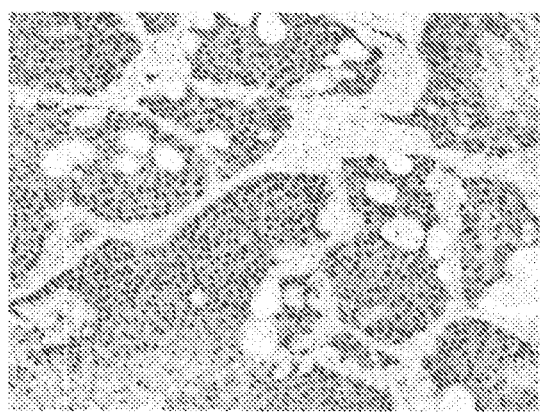

FIG. 47 shows a black and white version of the example of FIG. 15.

Figure 16:
FIG. 16 shows an example of the antibody cocktail p40 (M)+CK5 (RM) staining a specimen of lung ADC. Staining of p40 (brown, nuclear) and CK5 (red, cytoplasmic) may be reduced, or perhaps absent, in this sample.
Figure 48:
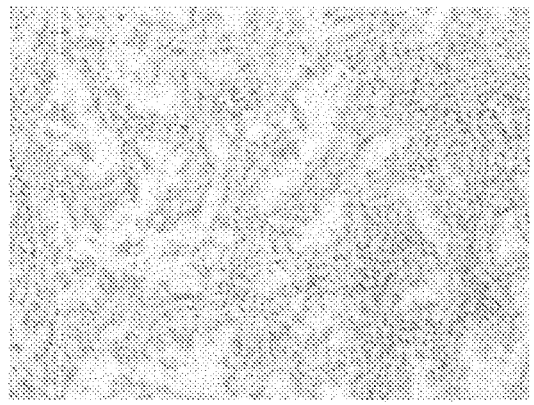

FIG. 48 shows a black and white version of the example of FIG. 16.

Figure 17:
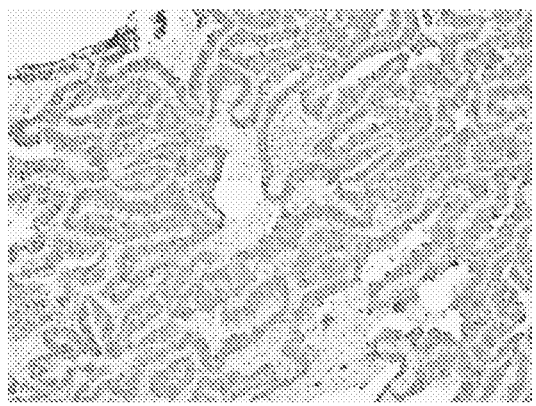
FIG. 17 shows an example of the antibody cocktail CK7+TRIM29 staining a specimen of lung ADC. Staining of CK7 (red) is cytoplasmic. Staining of TRIM29 (brown, cytoplasmic & membrane) may be reduced, or perhaps absent, in this sample.
Figure 49:
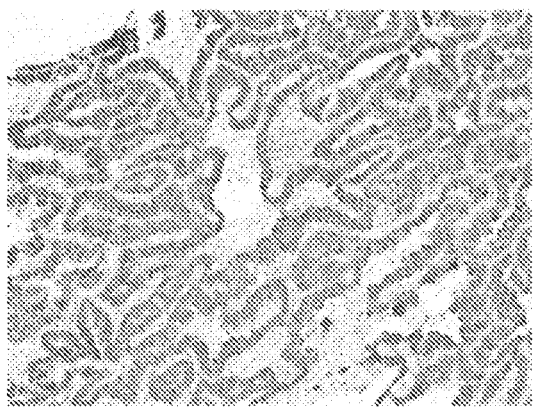

FIG. 49 shows a black and white version of the example of FIG. 17.

Figure 18:
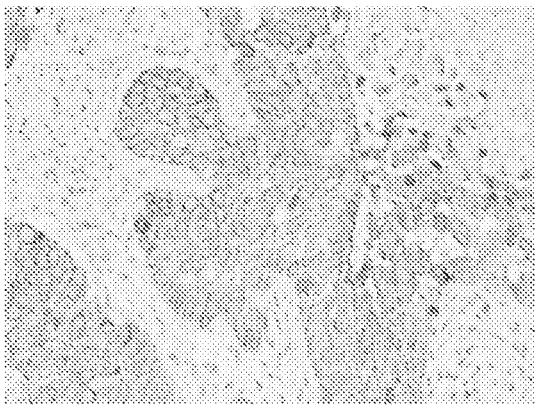
FIG. 18 shows an example of the antibody cocktail CK7+TRIM29 staining a specimen of lung SCC. Staining of TRIM29 (brown) is cytoplasmic and membrane. Staining of CK7 (red, cytoplasmic) may be reduced, or perhaps absent, in this sample.
Figure 50:

FIG. 50 shows a black and white version of the example of FIG. 18.

Figure 19:
FIG. 19 shows an example of the antibody cocktail CK7+TRIM29 staining a specimen of lung SCC. Staining of TRIM29 (brown) is cytoplasmic and membrane. Staining of CK7 (red, cytoplasmic) may be present in residual normal lung tissue.
Figure 51:
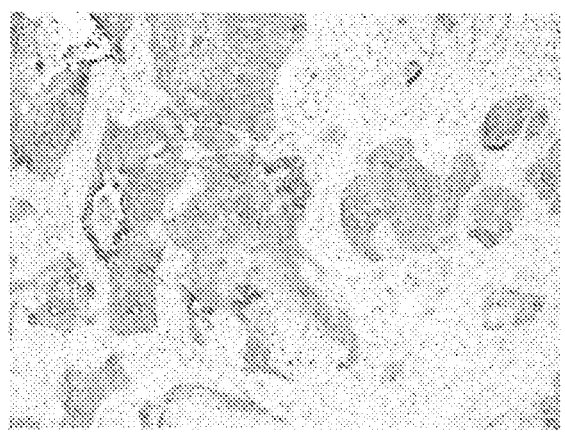

FIG. 51 shows a black and white version of the example of FIG. 19.

Figure 20:
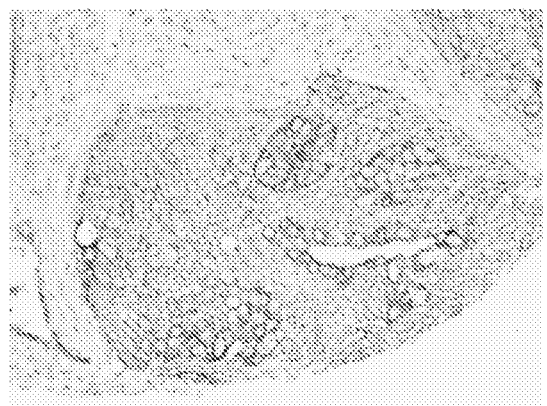
FIG. 20 shows an example of the antibody cocktail CK7+TRIM29 staining a specimen of lung adenosquamous carcinoma. Staining of TRIM29 (brown) is cytoplasmic and membrane and staining of CK7 (red) is cytoplasmic and/or membrane.
Figure 52:

FIG. 52 shows a black and white version of the example of FIG. 20.

Figure 21:
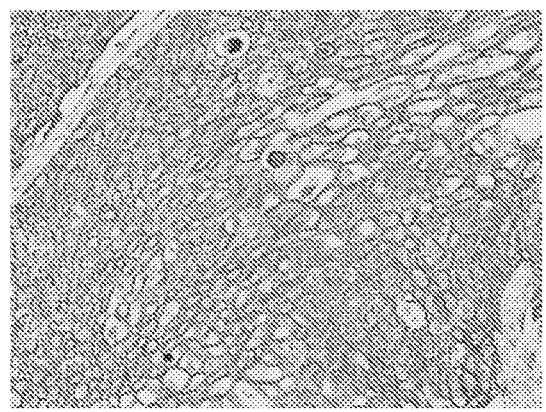
FIG. 21 shows an example of the antibody cocktail DSG3+CK5/Napsin A+TTF-1 staining a specimen of lung SCC. DSG-3 staining (brown) is membranous and CK5 staining (brown) is cytoplasmic. Napsin A staining (red, cytoplasmic) and TTF-1 staining (brown, nuclear) may be reduced, or perhaps restricted to normal lung tissue, in this sample.
Figure 53:
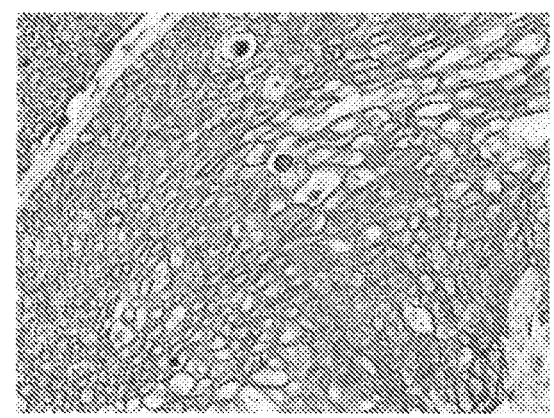

FIG. 53 shows a black and white version of the example of FIG. 21.

Figure 22:
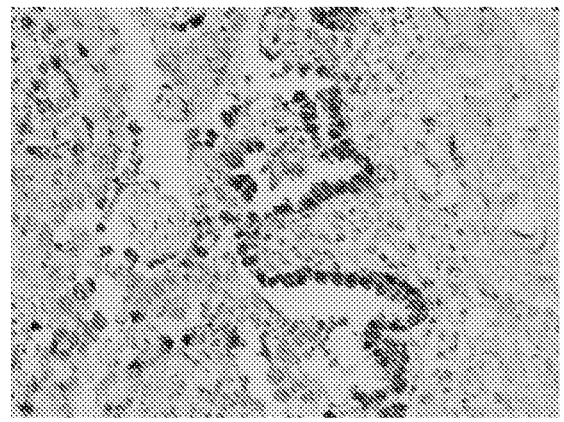
FIG. 22 shows an example of the antibody cocktail DSG3+CK5/Napsin A+TTF-1 staining a specimen of lung ADC. Napsin A staining (red) is cytoplasmic and TTF-1 staining (brown) is nuclear. DSG3 staining (brown, membranous) and CK5 staining (brown, cytoplasmic) may be reduced, or perhaps absent in this sample.
Figure 54:
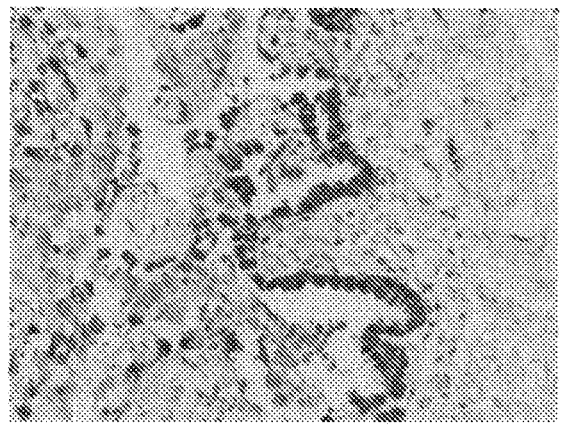

FIG. 54 shows a black and white version of the example of FIG. 22.

Figure 23:
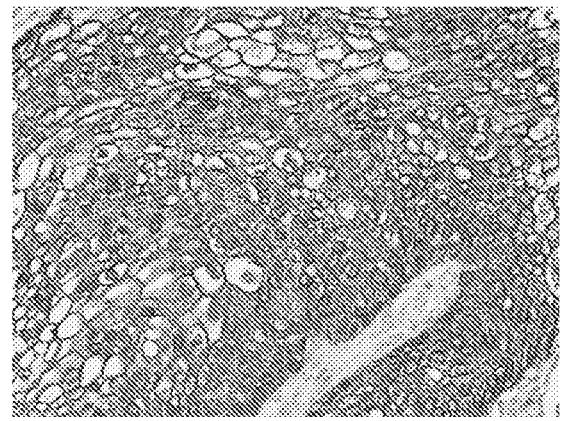
FIG. 23 shows an example of the antibody cocktail DSG3+CK5+p40/Napsin A+TTF-1 staining a specimen of lung SCC. DSG-3 staining (brown) is membranous; CK5 staining (brown) is cytoplasmic; and p40 staining (red) is nuclear. Napsin A staining (red, cytoplasmic) and TTF-1 staining (brown, nuclear) may be reduced, or perhaps absent, in this sample.
Figure 55:
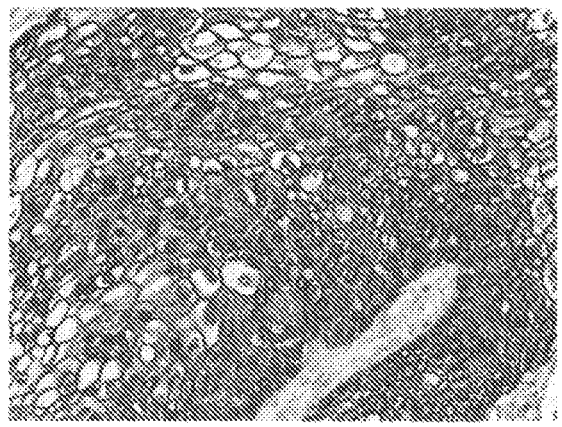

FIG. 55 shows a black and white version of the example of FIG. 23.

Figure 24:
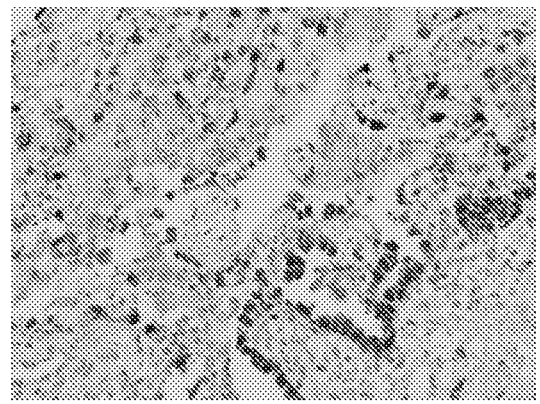
FIG. 24 shows an example of the antibody cocktail DSG3+CK5+p40/Napsin A+TTF-1 staining a specimen of lung ADC. Napsin A staining (red) is cytoplasmic and TTF-1 staining (brown) is nuclear. DSG3 staining (brown, membranous), CK5 staining (brown, cytoplasmic), and p40 staining (red, nuclear) may be reduced, or perhaps absent in this sample.
Figure 56:
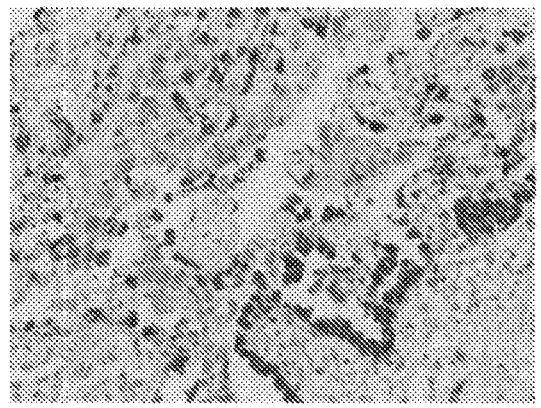

FIG. 56 shows a black and white version of the example of FIG. 24.

Figure 25:
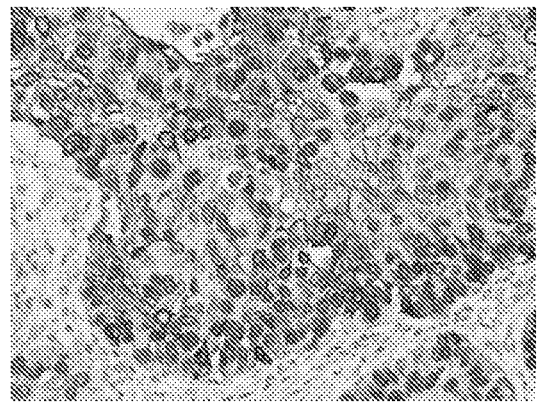
FIG. 25 shows an example of the antibody cocktail DSG3+CK5+p40 staining a specimen of lung SCC. DSG-3 staining (brown) is membranous; CK5 staining (brown) is cytoplasmic; and p40 staining (red) is nuclear.
Figure 57:
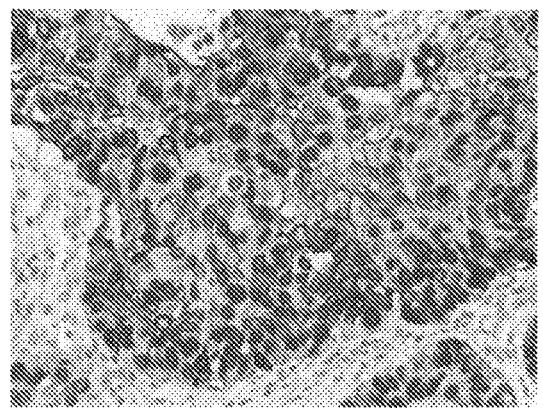

FIG. 57 shows a black and white version of the example of FIG. 25.

Figure 26:
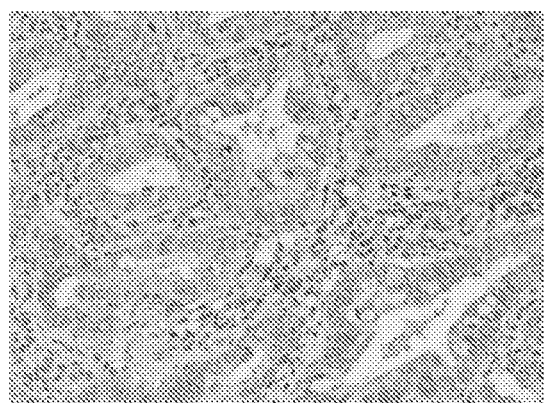
FIG. 26 shows an example of the antibody cocktail DSG3+CK5+p40 staining a specimen of lung ADC. DSG3 staining (brown, membranous), CK5 staining (brown, cytoplasmic), and p40 staining (red, nuclear) may be reduced, or perhaps absent in this sample.
Figure 58:
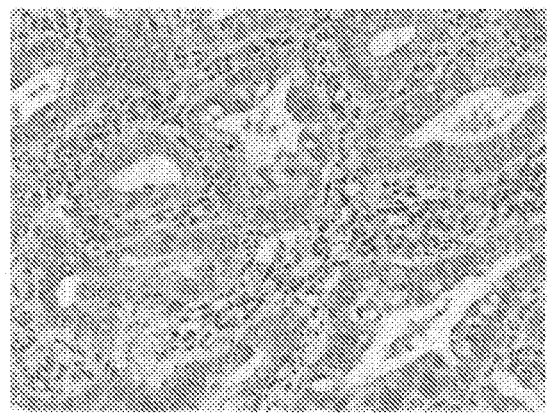

FIG. 58 shows a black and white version of the example of FIG. 26.

Figure 27:
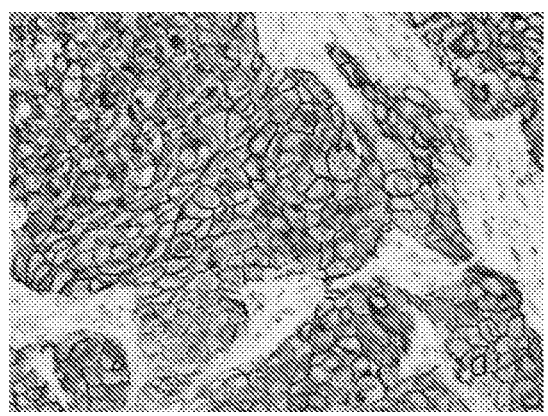
FIG. 27 shows an example of the antibody cocktail DSG-3+p40 staining a specimen of lung SCC. DSG-3 staining (brown) is membranous and p40 staining (red) is cytoplasmic.
Figure 59:
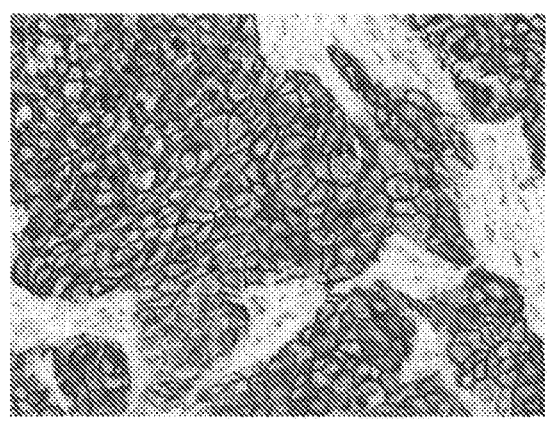

FIG. 59 shows a black and white version of the example of FIG. 27.

Figure 28:
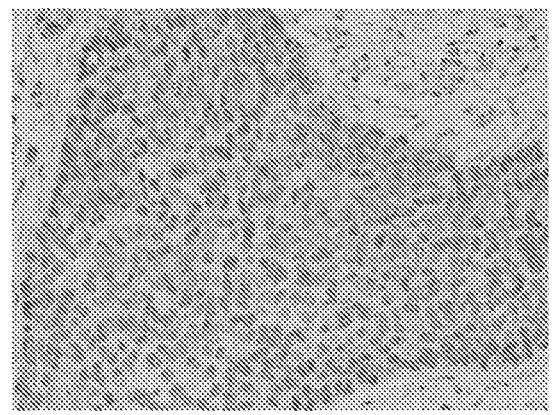
FIG. 28 shows an example of the antibody cocktail DSG-3+p40 staining a specimen of lung SCC. p40 staining (red) is cytoplasmic. Staining of DSG-3 (brown, membranous) is reduced, or perhaps absent in this sample.
Figure 60:
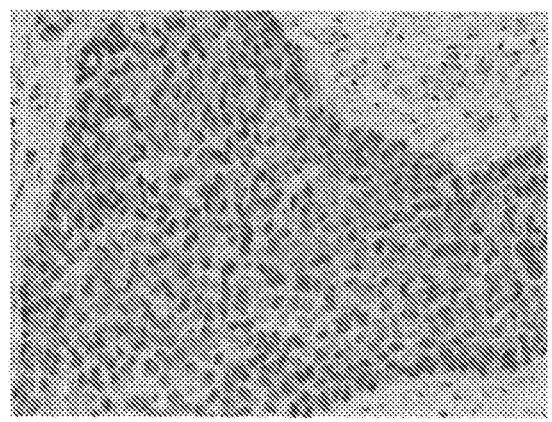

FIG. 60 shows a black and white version of the example of FIG. 28.

Figure 29:
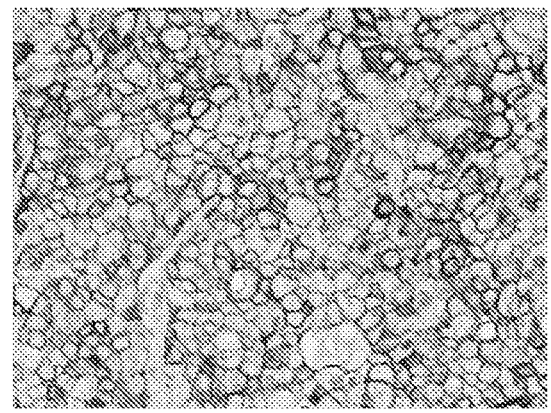
FIG. 29 shows an example of the antibody cocktail DSG-3+p40 staining a specimen of lung SCC. DSG-3 staining (brown) is membranous. Staining of p40 (red, nuclear) is reduced, or perhaps absent in this sample.
Figure 61:
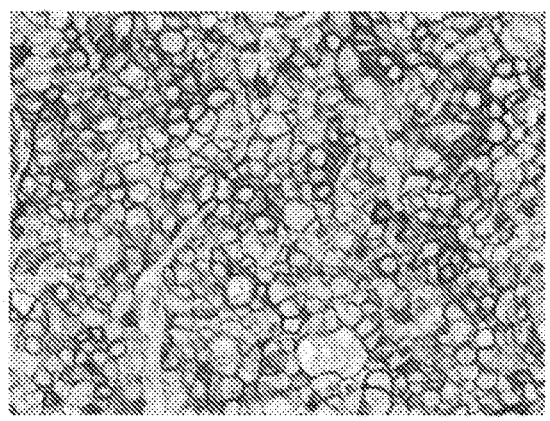

FIG. 61 shows a black and white version of the example of FIG. 29.

Figure 62:
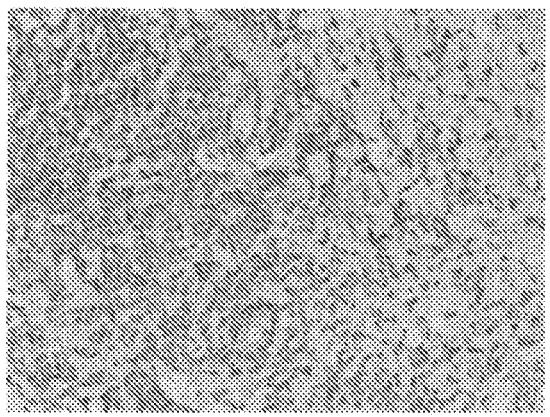

FIG. 62 shows a black and white version of the example of FIG. 30.

MODE(S) FOR CARRYING OUT THE INVENTION

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

In an embodiment of the present invention, a combination of one or more (e.g., at least one) primary antibodies may be used for the diagnosis of lung cancer, NSCLC, or the like. In other embodiments, antibodies may be used to evaluate the origin of a tumor as from the lung, or from an organ other than the lung. In certain embodiments, an antibody combination may be useful in identifying histologic subtypes of lung cancer, such as but not limited to SCC, ADC, and large cell carcinoma in NSCLC, or even small cell carcinomas. In embodiments, an antibody combination may be useful in distinguishing SCC and ADC in NSCLC. In certain embodiments the antibody combination may provide prognostic information, or perhaps be predictive of patient response to a particular therapy.

Embodiments of the present invention may include, but are not limited to lung cancer detection systems or even compositions comprising at least two primary antibodies or fragments thereof, wherein at least one primary antibody or fragment thereof specifically binds to squamous cell carcinoma (SCC); and wherein at least one primary antibody or fragment thereof specifically binds to adenocarcinoma (ADC). Embodiments of the present invention may include, but are not limited to lung cancer detection systems or even compositions comprising at least two primary antibodies or fragments thereof, wherein at least two primary antibodies each specifically binds to squamous cell carcinoma (SCC) or even comprising at least two primary antibodies or fragments thereof, wherein at least two primary antibodies each specifically binds to adenocarcinoma (ADC).

In certain embodiments, primary antibodies may be combined together in a single solution, as a "cocktail," perhaps suitable for simultaneous application to a specimen. Alternatively, the primary antibodies may be applied to the specimen in separate, sequential steps perhaps allowing non-simultaneous application to a sample. The antibodies may be derived from a mouse host or a rabbit host or the like. The antibodies may be monoclonal or polyclonal and may be isolated antibodies. In embodiments, an antibody cocktail may be used in a double-stain IHC procedure to produce two or more (e.g., at least two) colored stains that may identify the presence or absence of target protein antigens in the tissue specimen. For example, in embodiments where an antibody cocktail may be comprised of mouse and rabbit antibodies, a detection system may include an anti-mouse antibody conjugated to horseradish peroxidase (HRP) and perhaps even an anti-rabbit antibody conjugated to alkaline phosphatase (AP) may be used to produce the two-color stain. 3,3'-diaminobenzidine (DAB) may be used to produce a brown stain, perhaps facilitated by HRP, and it may identify the presence or absence, and/or location, of mouse antibodies bound in the specimen; Fast Red may be used to produce a fuchsia/red stain, perhaps facilitated by AP, and it may identify the presence or absence, and/or location, of rabbit antibodies in the specimen. In other embodiments, a detection system may include an anti-mouse antibody conjugated to AP and an anti-rabbit antibody conjugated to HRP which may be used to produce a two-color stain that may identify the presence or absence, and/or location of the mouse antibodies with a red stain and the rabbit antibodies with a brown stain, perhaps when Fast Red and DAB may be used as chromogens. In some embodiments, an antimouse antibody conjugated to HRP and perhaps an anti-rabbit antibody conjugated to AP may be applied to the specimen as a cocktail, in a single solution, or they may be applied in separate, sequential steps. In other embodiments, other chromogens known in the art may be used, for example, but not limited to 3-amino-9-ethylcarbazole (AEC), Fast Blue, 3,3',5,5'-tetramethylbenzidine (TMB), 5-Bromo-4-chloro-3-indolyl phosphate (BCIP), New fuschin, and the like. In other embodiments, glucose oxidase or perhaps β-galactosidase may be conjugated to an antibody for detection and perhaps used with chromogens such as 5-bromo-4-chloro-3-indolyl-β-D-galactopyranoside (X-Gal), 5-Bromo-3-indolyl β-D-galactopyranoside (Bluo-Gal), and the like.

An antibody-enzyme conjugate may include but is not limited to horseradish peroxidase (HRP), alkaline phosphate (AP), glucose oxidase, β-galactosidase, any combination thereof, or the like. A chromogen may include but is not limited to 3,3'-diaminobenzidine (DAB); Fast Red; 3-amino-9-ethylcarbazole (AEC); Fast Blue; 3,3',5,5'-tetramethylbenzidine (TMB); 5-Bromo-4-chloro-3-indolyl phosphate (BCIP); nitro blue tetrazolium (NBT); tetranitrobluetetrazolium (TNBT); New fuschin, 5-bromo-4-chloro-3-indolyl-β-D-galactopyranoside (X-Gal); 5-Bromo-3-indolyl β-D-galactopyranoside (Bluo-Gal); any combination thereof, or the like. Antibody-enzyme conjugates may include more than one (e.g., two or more) enzyme molecules conjugated to a single antibody, and perhaps even an intermediate linker may be used to connect the enzyme to the antibody. Antibody-enzyme conjugates known in the art as "polymer" detection systems, or "micropolymer" detection systems may be included in embodiments.

A primary antibody may be from a variety of host species, including, but not limited to mouse, rabbit, chicken, horse, rat, goat, sheep, or the like. The primary antibody may be monoclonal or polyclonal. In embodiments, mouse antibodies, including but not limited to DSG-3, CK5, TTF-1, p63, p40 and CK7, may be monoclonal. Hybridoma cells referred to as Anti-human p40 hybridoma clone BC28 Lot:011713 have been deposited at American Type Culture Collection (ATCC) in Manassas, Va. on Jan. 29, 2013 and has received ATCC Patent Deposit Designation No. PTA-120163. In embodiments, rabbit antibodies, including but not limited to p40, Napsin A, and TRIM29, may be monoclonal. In the case of monoclonal antibodies, it is understood that various antibody clones targeting the same antigen may be interchangeable in the present invention. The antibodies comprising the antibody-enzyme conjugates may be derived from a different host species, including, but not limited to mouse, rabbit, chicken, horse, rat, goat, sheep, or the like which may provide an anti-rabbit antibody, anti-mouse antibody, anti-chicken antibody, antihorse antibody, anti-rat antibody, anti-goat antibody, antisheep antibody, any combination thereof, or the like. The antibodies used in the antibody-enzyme conjugate may typically be chosen to bind primary antibodies from a specific host species. For example, in embodiments, a goat antimouse enzyme-antibody conjugate may be utilized for detecting mouse primary antibodies and a goat anti-rabbit enzyme-conjugate may be utilized for detecting rabbit primary antibodies. In embodiments, an antibody may include an antibody-enzyme conjugate and a primary antibody could be obtained from two different host species. Chromogens other than DAB and/or Fast Red may be used as well.

In embodiments, a biotin-streptavidin system, as known in the art, may be useful as a detection system. For example, a primary antibody may be conjugated with biotin, or perhaps even an intermediary antibody that binds the primary antibody may be conjugated with biotin. An avidin or streptavidin protein, perhaps conjugated with an enzyme, for example, but not limited to HRP or AP, may bind the biotin of the primary antibody, or perhaps the biotin of the intermediary antibody. DAB or Fast Red may be used to perhaps create a brown or red stain.

In embodiments, a primary antibody cocktail may include one or more (e.g., at least one) antibodies that may preferentially stain SCC, perhaps as well as one or more (e.g., at least one) antibodies that may preferentially stain ADC. In one embodiment, primary antibodies that may preferentially stain SCC may be from one host species (e.g. mouse or the like) and primary antibodies that may preferentially stain ADC may be derived from a different host species (e.g. rabbit or the like). In other embodiments, primary antibodies may be derived from the same host species and may even be used to evaluate the presence or absence of target protein antigens perhaps based on cellular localization of the resulting stain (e.g. nuclear, cytoplasmic, membranous, or the like).

In embodiments of the present invention, a primary antibody cocktail may include two or more (e.g., at least two) antibodies that may preferentially stain SCC. Alternatively, a primary antibody cocktail may include two or more (e.g., at least two) antibodies that may preferentially stain ADC.

Multiple alternatives to a double-staining method may be possible, including but not limited to the use of more than two (e.g., at least three) antibodies, the use of species other than mouse and rabbit, other chromogens and detection systems, a different order of detection steps, a different order of chromogen steps, a sequential or simultaneous application of selected reagents, and perhaps even modifications resulting in three or more (e.g., at least three) colors (which may require a denaturing step).

In some embodiments, an antibody cocktail of both mouse and rabbit antibodies may be used with an antibody-enzyme conjugate detection system that may not discriminate the antibodies by host species and may produce a single color stain. One such embodiment may consist of using a detection system which may include an anti-rabbit antibody conjugated to HRP and may even include an anti-mouse antibody conjugated to HRP, perhaps followed by DAB to produce a brown stain, which may identify the presence or absence, and/or location of the mouse and rabbit antibodies, or the like. In an alternative embodiment, an intermediary antibody may be used. For example, with a primary antibody cocktail which may include mouse and rabbit antibodies, a detection method may include a rabbit anti-mouse antibody, perhaps followed by an anti-rabbit antibody conjugated to HRP, which may produce a single-color stain with DAB, or the like. In such embodiments, a location of specific antibodies may be identified by known cellular localization or their target antigens or the like. Additionally, in some embodiments, specific identification of each antibody may not be necessary in determining the diagnosis of the specimen or identifying the histologic subtype. Particularly, in embodiments where the antibody cocktail may include antibodies that preferentially stain one histologic subtype, it may be desirable to use a single antibody-enzyme conjugate which may produce a single color stain.

Methods of the present invention may be useful for evaluating well differentiated, moderately differentiated, or perhaps even poorly differentiated carcinoma. In embodiments, a method may be useful for the evaluation of poorly differentiated carcinoma.

Various combinations of primary antibodies may be useful in various embodiments of the present invention. Numerous antibodies are known in the art which may be useful for diagnosis of cancer, such as lung cancer, perhaps by IHC. These antibodies may be useful in distinguishing histologic subtypes of NSCLC, because each antibody may result in a distinctive staining pattern, which may be useful to a pathologist in identifying histologic subtype. The particular combinations of antibodies that are useful for such purposes are not known.

Antibodies that may be useful for identifying lung SCC may include, but are not limited to: DSG-3, CK5, p63, p40, TRIM29, or the like (e.g., anti-Desmoglein 3 (anti-DSG-3) antibody, anti-CK5 antibody, anti-p63 antibody, anti-p40 antibody, and anti-TRIM29 antibody, or the like). Antibodies that may be useful for identifying lung ADC may include, but are not limited to: Napsin A, TTF-1, CK7, or the like (e.g., anti-Napsin A antibody, anti-TTF-1 antibody, and anti-CK7 antibody, or the like).

FIG. 31 shows a schematic summary of various embodiments of the present invention including a detection system or even a kit (5) which may provide an antibody, at least two antibodies, fragment(s) thereof, or a portion thereof, perhaps in a composition, primary antibody combination, or even in a cocktail, the at least one antibody (1) or the like may be contacted with a biological sample (2) to form at least one antibody-antigen complex (3) which may then be detected with a detector (4). A detector may include at least one antibody-enzyme conjugate, at least one chromogen, biotin-streptavidin system, or the like.

As but one example of a method, embodiments of the present invention may provide obtaining tissue from an animal or human to be tested (6), fixing or freezing said tissue (7), treating said fixed or frozen tissue to unmask epitopes (8), contacting a tissue with an antibody or fragment thereof, or at least two antibodies, as discussed herein, in an amount and under conditions such that an antibody, antibodies, or fragments thereof binds to a specific protein if the protein is present in said tissue (9); and perhaps even detecting the presences of said bound antibodies (10) as discussed herein, as schematically represented in FIG. 32.

Table 1 lists several examples of antibody combinations that may be useful in any of the embodiments of the present invention. In particular, Table 1 suggests a staining pattern that may be observed with the listed antibody combination, as well as perhaps how an antibody combination may be useful for clinical diagnosis, particularly in identifying histologic subtypes of NSCLC, including, but not limited to SCC and ADC. The host species listed for the antibody in each combination are provided as non-limiting examples and antibodies that bind the same antigen, but may have been derived form a different host species, or may bind a different epitope, may also be useful in various embodiments. For example, in embodiments, p63 may be used in place of p40 or the like. In embodiments, antibodies may be chosen that perhaps bind fewer antigens and may be more specific. As a non-limiting example, CK5 may be used instead of CK5/6.

TABLE 1

| Antibody Combination and (Host Species) | Possible Staining Pattern (cellular localization, stain color*) | Possible Diagnostic Utility | Detection System Used in Example and Figure No. |
| --- | --- | --- | --- |
| DSG-3 (Mouse) CK5 (Mouse) Napsin A (Rabbit) | DSG-3 (Membrane, Brown) CK5 (Cytoplasmic, Brown) Napsin A(Cytoplasmic, Red) | DSG-3 and/or CK5 staining may be observed in SCC; Napsin A staining may be observed in ADC. | DS#2 FIGS. 1-4, 33-36 |
| p40 (Rabbit) TTF-1 (Mouse) | p40 (Nuclear, Brown) TTF-1 (Nuclear, Red) | p40 staining may be observed in SCC; TTF-1 staining may be observed in ADC. | DS#1 FIGS. 5-8, 37-40 |
| DSG-3 (Mouse) p40 (M) (Mouse) Napsin A (Rabbit) | DSG-3 (Membrane, Brown) p40 (M) (Nuclear, Brown) Napsin A(Cytoplasmic, Red) | DSG-3 and/or p40 staining may be observed in SCC; Napsin A staining may be observed in ADC. | DS#2 FIGS. 9-13, 41-45 |
| DSG-3 (Mouse) p40 (M) (Mouse) | DSG-3 (Membrane, Brown) p40 (M) (Nuclear, Brown) | DSG-3 and/or p40 staining may be observed in SCC. | Goat anti-mouse HRP FIG. 14, 46 |

TABLE 1-continued

| Antibody Combination and (Host Species) | Possible Staining Pattern (cellular localization, stain color*) | Possible Diagnostic Utility | Detection System Used in Example and Figure No. |
|---|---|---|---|
| p40 (M) (Mouse) CK5 (Rabbit) | p40 (Nuclear, Brown) CK5 (Cytoplasmic, Red) | CK5 and/or p40 staining may be observed in SCC. | DS#2 FIGS. 15-16, 47-48 |
| Trim29 (Rabbit) CK7 (Mouse) | Trim29 (Cytoplasmic, Brown) CK7 (Cytoplasmic, Red) | TRIM29 staining may be observed in SCC; CK7 staining may be observed in ADC. | DS#1 FIGS. 17-20, 48-52 |
| DSG-3 (Mouse) CK5 (Mouse) Napsin A (Rabbit) TTF-1 (Mouse) | DSG-3 (Membrane, Brown) CK5 (Cytoplasmic, Brown) Napsin A (Cytoplasmic, Red) TTF-1 (Nuclear, Brown) | DSG-3 and/or CK5 staining may be observed in SCC; Napsin A and/or TTF-1 staining may be observed in ADC. | DS#2 FIGS. 21-22, 53-54 |
| DSG-3 (Mouse) CK5 (Mouse) p40 (Rabbit) Napsin A (Rabbit) TTF-1 (Mouse) | DSG-3 (Membrane, Brown) CK5 (Cytoplasmic, Brown) p40 (Nuclear, Red) Napsin A (Cytoplasmic, Red) TTF-1 (Nuclear, Brown) | DSG-3 and/or CK5 and/or p40 staining may be observed in SCC; Napsin A and/or TTF-1 staining may be observed in ADC. | DS#2 FIGS. 23-24, 55-56 |
| DSG-3 (Mouse) CK5 (Mouse) p40 (Rabbit) | DSG-3 (Membrane, Brown) CK5 (Cytoplasmic, Brown) p40 (Nuclear, Red) | DSG-3 and/or CK5 and/or p40 staining may be observed in SCC. | DS#2 FIGS. 25-26, 57-58 |
| DSG-3 (Mouse) p40 (Rabbit) | DSG-3 (Membrane, Brown) p40 (Nuclear, Red) | DSG-3 and/or p40 staining may be observed in SCC. | DS#2 FIGS. 27-30, 59-62 |

*The listed color of each stain may be a result of a detection system that may include an anti-mouse antibody perhaps conjugated to HRP and even an anti-rabbit antibody perhaps conjugated to AP, perhaps even with DAB and Fast Red as chromogens, which may result in brown staining for mouse antibodies and red staining for rabbit antibodies (referred to as DS#2). Alternatively, the detection system may include an anti-mouse antibody perhaps conjugated to AP and even an anti-rabbit antibody perhaps conjugated to HRP, perhaps even with DAB and Fast Red as chromogens, which may result in red staining for mouse antibodies and brown staining for rabbit antibodies (referred to as DS#1). In some instances, two colors may not be necessary because the antigens may be distinguished by cellular localization of staining, or perhaps it is not diagnostically significant to determine which antigen is staining. Other color combinations may be obtained using other detection systems or chromogens and all are meant to be included in this disclosure.

A primary antibody combination for use with biological samples may include but is not limited to anti-DSG-3 antibody or fragment thereof, anti-CK5 antibody or fragment thereof, and anti-Napsin A antibody or fragment thereof; anti-p40 antibody or fragment thereof, and anti-TTF-1 antibody or fragment thereof; anti-DSG-3 antibody or fragment thereof, anti-p40 antibody or fragment thereof, and anti-Napsin A antibody or fragment thereof; anti-DSG-3 antibody or fragment thereof, and anti-p40 antibody or fragment thereof; anti-p40 antibody or fragment thereof, and anti-CK5 antibody or fragment thereof; anti-CK7 antibody or fragment thereof, and anti-TRIM29 antibody or fragment thereof; anti-DSG-3 antibody or fragment thereof, anti-CK5 antibody or fragment thereof, anti-Napsin A antibody or fragment thereof, and anti-TTF-1 antibody or fragment thereof; anti-DSG-3 antibody or fragment thereof, anti-CK5 antibody or fragment thereof, anti-p40 antibody or fragment thereof, anti-Napsin A antibody or fragment thereof, and anti-TTF-1 antibody or fragment thereof; anti-DSG-3 antibody or fragment thereof, anti-CK5 antibody or fragment thereof, and anti-p40 antibody or fragment thereof; anti-DSG-3 mouse antibody or fragment thereof, anti-CK5 mouse antibody or fragment thereof, anti-Napsin A rabbit antibody or fragment thereof; anti-p40 rabbit antibody or fragment thereof, and anti-TTF-1 mouse antibody or fragment thereof; anti-DSG-3 mouse antibody or fragment thereof, anti-p40 mouse antibody or fragment thereof, and anti-Napsin A rabbit antibody or fragment thereof; anti-DSG-3 mouse antibody or fragment thereof, and anti-p40 mouse antibody or fragment thereof; anti-p40 mouse antibody or fragment thereof, and anti-CK5 rabbit antibody or fragment thereof; anti-TRIM29 rabbit antibody or fragment thereof, and anti-CK7 mouse antibody or fragment thereof; anti-DSG-3 mouse antibody or fragment thereof, anti-CK5 mouse antibody or fragment thereof, anti-Napsin A rabbit antibody or fragment thereof, and anti-TTF-1 mouse antibody or fragment thereof; anti-DSG-3 mouse antibody or fragment thereof, anti-CK5 mouse antibody or fragment thereof, anti-p40 rabbit antibody or fragment thereof, anti-Napsin A rabbit antibody or fragment thereof, and anti-TTF-1 mouse antibody or fragment thereof; anti-DSG-3 mouse antibody or fragment thereof, anti-CK5 mouse antibody or fragment thereof, and anti-p40 rabbit antibody or fragment thereof; anti-DSG-3 mouse antibody or fragment thereof, and anti-p40 rabbit antibody or fragment thereof, or the like.

It may be well understood by those skilled in the art that it may be reasonably anticipated that a particular antibody combination may not stain all specimens of a particular histologic subtype. It may be understood that a particular antibody combination may stain perhaps only a subset of the expected specimens, yet such an antibody combination or method may be advantageous for other reasons, such as for example, specificity or the like.

Classification of histologic subtype in lung cancer has been shown to be both prognostic of clinical outcomes, as well as predictive of outcome in patients treated with certain therapeutic agents. In certain embodiments, the presence or absence of a particular target antigen, or perhaps the intensity of staining observed for an antigen, may be useful as a prognostic tool in predicting clinical outcomes, or predictive of response to a particular therapy. For example, the reduction or absence of DSG3 (negative staining) has been associated with shorter survival times for lung cancer patients, compared to patients that express higher levels of DSG3 (positive staining). The reduction or absence of Napsin A has also been associated with reduced survival time.

The present invention may provide kits for immunoassaying a sample containing an antibody cocktail, detection reagents, other reagents useful for the immune assay, and perhaps even instructions to use the kit.

Example IHC Method Using DSG-3, CK5 and Napsin A:

Immunohistochemistry using a cocktail of antibodies such as the mouse monoclonal antibodies DSG-3 [BC11] and CK5 [EP1601Y] and rabbit polyclonal Napsin A may be performed on formalin-fixed paraffin embedded (FFPE) tissue samples using procedures generally known to those in the art, as generally exemplified by the following non-limiting examples (e.g., washes with Tris-buffered saline, pH about 7.6, between steps):

1) Sections (~5 µm) of formalin fixed paraffin-embedded tissues may be mounted on commercially available microscope slides perhaps coated with poly-L-lysine.
2) Sections may be deparaffinized (perhaps using xylenes or even a xylene-substitute or the like) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Reveal Decloaker, Decloaking Chamber; Biocare Medical) and may be heated to about 125° C. for about 30 seconds. [Other antigen retrieval methods known to those skilled in the art (e.g., steamer, microwave oven, enzyme, or the like) may also be utilized.] Tissues may be allowed to cool for about 10 minutes and then may be rinsed with deionized water.
4) The primary antibody cocktail, comprised of DSG-3, CK5 and Napsin A may be applied in a phosphate-buffered solution (pH about 6.0) with bovine serum albumin as carrier protein for about 30 minutes. [Other buffered solutions, other pH's, with other additives known to those skilled in the art (e.g., Tris buffer, pH about 7.4, casein) may also be utilized.]
5) Detection of the DSG-3, CK5 and Napsin A primary antibodies may be performed perhaps with a cocktail of goat anti-mouse antibody conjugated to HRP and goat anti-rabbit antibody conjugated to AP (MACH 2 Double Stain 2, Biocare Medical) perhaps applied for about 30 minutes.
6) In perhaps a next detection step, 3,3'-diaminobenzidine (DAB) in buffer perhaps containing about 0.02% hydrogen peroxide (Betazoid DAB, Biocare Medical) may be applied. The reaction of DAB through an HRP-mediated mechanism may result in precipitation of a brown, chromogenic product (e.g., a stain), perhaps allowing identification of sites of expression of the protein antigen targets of the mouse primary antibodies (DSG-3, CK5).
7) In perhaps a final detection step, a solution of a Fast Red diazonium salt (e.g., Fast Red KL) and a naphthol phosphate (e.g., Naphthol AS-TR phosphate, disodium salt) in a buffer perhaps with a pH about 8.0 to about 8.5 may be applied. Perhaps the cleavage of the phosphate from the naphthol phosphate through an AP-mediated mechanism may produce a product that may react with a Fast Red diazonium salt which may produce a red/fuchsia chromogenic product (e.g., a stain), perhaps allowing identification of the sites of expression of the protein antigen targets of the rabbit primary antibody (Napsin A).
8) Slides may be briefly counterstained perhaps in a modified Mayer's hematoxylin.

Each of the various steps, individually or in any combination, of the Example IHC Method may be generally applicable to any of the antibody combination examples listed in Table 1, as well as other embodiments of the present invention. Methods of the present invention may be performed on an automated staining device, through a manual method, or any other effectively equivalent method, as may be known by those skilled in the art.

Results of IHC Staining with DSG-3, CK5 and Napsin A:

Using the above protocol, FFPE tissues may be stained with a cocktail of DSG-3, CK5 and Napsin A. Examples of staining of SCC are shown in FIGS. 1, 2, 33 and 34. The presence of DSG-3 and/or CK5 antibodies may result in the brown staining. No red staining may have been observed, suggesting perhaps an absence of Napsin A protein. Examples of staining of ADC are shown in FIGS. 3, 4, 35 and 36. The presence of Napsin A antibodies may result in red staining. No brown staining may have been observed, suggesting perhaps the absence of DSG-3 and CK5.

Results of IHC Staining with p40 and TTF-1:

Using the above protocol, with detection system DS#1, FFPE tissues may be stained with a cocktail of p-40 (e.g., rabbit polyclonal) and TTF-1 (e.g., mouse monoclonal [8G7G3/1]). Examples of staining of SCC are shown in FIGS. 5, 6, 37 and 38. The presence of p40 antibodies may result in the brown staining. No red staining may have been observed, suggesting perhaps an absence of TTF-1 protein. Examples of staining of ADC are shown in FIGS. 7, 8, 39 and 40. The presence of TTF-1 antibodies may result in red staining. No brown staining may have been observed, suggesting perhaps the absence of p40.

Results of IHC Staining with DSG-3, p40 (M) and Napsin A:

Using the above protocol, FFPE tissues may be stained with a cocktail of DSG-3, p40 (M) (e.g., mouse monoclonal [BC28]) and Napsin A. Examples of staining of ADC are shown in FIGS. 9, 10, 41 and 42. The presence of Napsin A may result in the red staining. Brown staining from p40 or DSG-3 may be reduced, or absent (e.g., see FIGS. 9 and 41), or even restricted to residual normal lung tissue (e.g., see FIGS. 10 and 42). Examples of staining of ADC are shown in FIGS. 11, 12, 13, 43, 44, and 45. The presence of DSG-3 or p40 antibodies may result in brown staining. Red staining of Napsin A may be reduced or absent, or perhaps restricted to residual normal lung tissue.

Results of IHC Staining with DSG-3 and p40 (M):

Using the above protocol, with a detection system of goat anti-mouse HRP, FFPE tissues may be stained with a cocktail of DSG-3 and p40 (M). Examples of staining of SCC are shown in FIGS. 14 and 46. The presence of DSG-3 and/or CK5 antibodies may result in the brown staining.

Results of IHC Staining with p40 (M) and CK5 (RM):

Using the above protocol, FFPE tissues may be stained with a cocktail of p40 (M) and CK5 (RM) (e.g., rabbit monoclonal [EP1601Y]). Examples of staining of SCC are shown in FIGS. 15 and 47. The presence of p40 (M) antibodies may result in the brown staining and the presence of CK5 (RM) antibodies results in the red staining. Examples of staining of ADC are shown in FIGS. 16 and 48. No brown or red staining may be observed, suggesting perhaps the absence of p40 and CK5.

Results of IHC Staining with CK7 and TRIM29:

Using the above protocol, with detection system DS#1, FFPE tissues may be stained with a cocktail of CK7 (e.g., mouse monoclonal, [OV-TL 12/30]) and TRIM29 (e.g., rabbit polyclonal). Examples of staining of ADC are shown in FIGS. 17 and 49. The presence of CK7 antibodies may result in the red staining. No brown staining may be observed, suggesting perhaps an absence of TRIM29 protein. Examples of staining of SCC are shown in FIGS. 18, 19, 50, and 51. The presence of TRIM29 antibodies may result in brown staining. Red staining from CK7 may also be observed in residual normal lung tissue. FIGS. 20 and 52 show examples of staining of adenosquamous lung carcinoma. In this example, both red and brown staining may be observed, suggesting the presence of both CK7 and TRIM29 proteins.

Alternative Example IHC Method Using DSG-3, CK5 and Napsin A:

Alternatively, IHC may be performed essentially as described in the above example with the difference of applying reagents in separate, sequential steps, rather than as cocktails. In particular, the primary antibodies and/or the detection enzyme-antibody conjugates may be applied in separate steps.

For example, staining with DSG-3, CK5 and Napsin A may be performed on formalin-fixed paraffin embedded (FFPE) tissue samples using procedures generally known to those in the art, as generally exemplified by the following non-limiting examples (e.g. washes with Tris-buffered saline, pH about 7.6, between steps):

1) Sections (~5 μm) of formalin fixed paraffin-embedded tissues may be mounted on commercially available microscope slides perhaps coated with poly-L-lysine.
2) Sections may be deparaffinized (using xylenes or a xylene-substitute) and may be rehydrated perhaps through a series of alcohol/water solutions, perhaps followed by blocking of endogenous peroxidases perhaps with about 3% hydrogen peroxide solution.
3) Samples may be subjected to heat-induced antigen retrieval using a citrate buffer in a pressure cooker (Reveal Decloaker, Decloaking Chamber; Biocare Medical) and may be heated to about 125° C. for about 30 seconds. [Other antigen retrieval methods known to those skilled in the art (e.g. steamer, microwave oven, enzyme, or the like) may also be acceptable.] Tissues may be allowed to cool for about 10 minutes and then may be rinsed with deionized water.
4) The first primary antibody, DSG-3, may be applied in a phosphate-buffered solution (pH about 6.0) with bovine serum albumin as carrier protein for about 30 minutes. [Other buffered solutions, other pH's, with other additives known to those skilled in the art (e.g. Tris buffer, pH about 7.4, casein) may also be acceptable.]
5) The second primary antibody, CK5, may be applied in a phosphate-buffered solution (pH about 6.0) with bovine serum albumin as carrier protein for about 30 minutes. [Other buffered solutions, other pH's, with other additives known to those skilled in the art (e.g. Tris buffer, pH about 7.4, casein) may also be acceptable.]
6) The third primary antibody, Napsin A, may be applied in a phosphate-buffered solution (pH about 6.0) with bovine serum albumin as carrier protein for about 30 minutes. [Other buffered solutions, other pH's, with other additives known to those skilled in the art (e.g. Tris buffer, pH about 7.4, casein) may also be acceptable.]
7) A goat anti-mouse antibody conjugated to HRP may be applied (MACH 2 Mouse HRP Polymer, Biocare Medical), perhaps for 30 minutes.
8) A goat anti-mouse antibody conjugated to AP may be applied (MACH 2 Mouse AP Polymer, Biocare Medical), perhaps for 30 minutes.
9) In perhaps a next detection step, 3,3'-diaminobenzidine (DAB) in buffer perhaps containing about 0.02% hydrogen peroxide (Betazoid DAB, Biocare Medical) may be applied. The reaction of DAB through a HRP-mediated mechanism may result in precipitation of a brown, chromogenic product (i.e. a stain), perhaps allowing identification of sites of expression of the protein antigen targets of the mouse primary antibodies (DSG-3, CK5).
10) In perhaps a final detection step, a solution of a Fast Red diazonium salt (e.g. Fast Red KL) and a naphthol phosphate (e.g. Naphthol AS-TR phosphate, disodium salt) in a buffer perhaps with a pH about 8.0 to 8.5 may be applied. Perhaps the cleavage of the phosphate from the naphthol phosphate through an AP-mediated mechanism may produce a product that reacts with the Fast Red diazonium salt which may produce a red/fuchsia chromogenic product (i.e. a stain), perhaps allowing identification of the sites of expression of the protein antigen targets of the rabbit primary antibody (Napsin A).
11) Slides may be briefly counterstained perhaps in a modified Mayer's hematoxylin.

Results of IHC Staining with DSG-3, CK5, Napsin A and TTF-1:

Using the above protocol, FFPE tissues may be stained with a cocktail of DSG-3, CK5, Napsin A, and TTF-1. Examples of staining of SCC are shown in FIGS. 21 and 53. The presence of DSG-3 or CK5 antibodies results in membranous or cytoplasmic brown staining, respectively. Red staining of Napsin A may be reduced or absent, or perhaps restricted to residual normal lung tissue. Brown staining of TTF-1 may be reduced, or perhaps absent. Examples of staining of ADC are shown in FIGS. 22 and 54. The presence of Napsin A may result in the red cytoplasmic staining. Nuclear brown staining may result from the presence of TTF-1. Membranous or cytoplasmic brown staining due to DSG3 or CK5, respectively, may be reduced, or absent.

Results of IHC Staining with DSG-3, CK5, p40, Napsin A and TTF-1:

Using the above protocol, FFPE tissues may be stained with a cocktail of DSG-3, CK5, p40, Napsin A, and TTF-1. Examples of staining of SCC are shown in FIGS. 23 and 55. The presence of DSG-3 (membranous) and/or CK5 (cytoplasmic) antibodies results in brown staining. The presence of p40 (nuclear) may result in red staining. Red staining of Napsin A (cytoplasmic) may be reduced or absent, or perhaps restricted to residual normal lung tissue. Brown staining of TTF-1 (nuclear) may be reduced, or perhaps absent. Examples of staining of ADC are shown in FIGS. 24 and 56. The presence of Napsin A may result in the red cytoplasmic staining. Nuclear brown staining may result from the presence of TTF-1. Brown staining due to the presence of DSG3 (membranous) or CK5 (cytoplasmic), as well as red staining due to the presence of p40 (nuclear) may be reduced, or perhaps absent.

Results of IHC Staining with DSG-3, CK5, and p40:

Using the above protocol, FFPE tissues may be stained with a cocktail of DSG-3, CK5, and p40. Examples of staining of SCC are shown in FIGS. 25 and 57. The presence of DSG-3 (membranous) and/or CK5 (cytoplasmic) antibodies results in brown staining. The presence of p40 (nuclear) may result in red staining. Examples of staining of ADC are shown in FIGS. 26 and 58. Brown staining due to the presence of DSG3 (membranous) or CK5 (cytoplasmic), as well as red staining due to the presence of p40 (nuclear) may be reduced, or perhaps absent.

Results of IHC Staining with DSG-3 and p40:

Using the above protocol, FFPE tissues may be stained with a cocktail of DSG-3 and rabbit polyclonal antibody p40. Examples of staining of SCC are shown in FIGS. 27-29 and 59-61. FIGS. 27 and 50 are an example of a specimen that may stain for both DSG-3 and p40. The presence of DSG-3 may result in brown, membranous staining. The presence of p40 may result in red, nuclear staining. FIGS. 28 and 60 are an example of a specimen that may be positive for p40 (red, nuclear), but may be negative for DSG-3 (brown, membranous). Similarly, FIGS. 29 and 61 are an example of a specimen that may be positive for DSG-3 (brown, membranous), but may be negative for p40 (red, nuclear). Additionally, FIGS. 30 and 62 are an example of ADC. In this specimen, staining of DSG-3 and/or p40 may be reduced, or perhaps absent.

An antibody marker may not stain all specimens of a particular subtype. It is expected and perhaps typical that the sensitivity of a particular antibody can be less than 100%. Together, FIGS. 27-29 and 59-62 are examples of an important feature of many embodiments of the present invention. That is, an increase in sensitivity may be achieved by using two or more (e.g., at least two) markers for the same histologic subtype (in this example, for SCC) in the same cocktail. FIGS. 27 and 59 are an example in which both DSG-3 and p40 markers were positive. However, FIGS. 28 and 60 are an example in which only the p40 marker was positive and the DSG-3 marker was negative. Similarly, FIGS. 29 and 61 are an example in which the DSG-3 marker was positive and the p40 marker was negative. Clearly, there is an advantage to using multiple markers on the same specimen to increase sensitivity. If only one marker had been used in the specimen of FIG. 28, 29, 60 or 61, an inaccurate result may have been obtained. Specifically, if the specimen of FIGS. 28 and 60 had been stained with only DSG-3, SCC may have been ruled out as a diagnosis, which may have been incorrect, as the positive staining with p40 is indicative of SCC. Likewise, if the specimen of FIGS. 29 and 61 had been stained with only p40, SCC may have been ruled out as a diagnosis, which may have been incorrect, as the positive staining with DSG-3 is indicative of SCC. When used together, DSG-3 and p40 may be more sensitive for detecting SCC than either antibody alone.

Combinations of antibodies may also offer advantages with increased specificity. While staining with a particular antibody (e.g., p40) may be consistent with a particular histologic subtype (e.g., SCC), said staining may also be consistent with other subtypes (e.g., ADC), but perhaps with decreased frequency. For example, in the example of FIGS. 28 and 60, positive staining of p40 may be consistent with a diagnosis of SCC; however, a small percentage of ADC cases may also be positive for p40. In this case, the results of staining with antibodies known to be consistent with ADC may be helpful. For example, if Napsin A and/or TTF-1 were found to be negative (in addition to the positive staining of p40) in the example of FIGS. 28 and 60, a determination of SCC may be made, perhaps with greater confidence by the pathologist. Alternatively, if Napsin A and/or TTF-1 were found to be positive in this specimen, the possibility of the specimen being ADC may remain, and further investigation may be needed before diagnosis. Antibody cocktails including multiple antibodies (e.g., two, three, four, five, or perhaps more) antibodies may be useful for achieving improved specificity, or perhaps even improved sensitivity.

The advantages of increased sensitivity demonstrated by FIGS. 27-29 and 59-61 should be considered to apply to other cocktails and other embodiments of the present invention. Many of the disclosed antibody combinations may result in increased sensitivity for SCC and/or ADC than the antibodies individually.

Clauses of the present invention may include:

Clause 1. A lung cancer detection system comprising:
at least two primary antibodies or fragments thereof, wherein at least one primary antibody or fragment thereof specifically binds to squamous cell carcinoma (SCC); and
wherein at least one primary antibody or fragment thereof specifically binds to adenocarcinoma (ADC).

Clause 2. A lung cancer detection system comprising at least two primary antibodies or fragments thereof, wherein at least two primary antibodies each specifically binds to squamous cell carcinoma (SCC).

Clause 3. A lung cancer detection system comprising at least two primary antibodies or fragments thereof, wherein at least two primary antibodies each specifically binds to adenocarcinoma (ADC).

Clause 4. A lung cancer detection system according to clause 2 or any other clause and further comprising:
at least one primary antibody or fragment thereof which specifically binds to adenocarcinoma (ADC).

Clause 5. A lung cancer detection system according to clause 3 or any other clause and further comprising:
at least one primary antibody or fragment thereof which specifically binds to squamous cell carcinoma (SCC).

Clause 6. A lung cancer detection system according to clause 2, 3, 4, or 5 or any other clause wherein said antibodies comprise an antibody cocktail allowing simultaneous application to a sample.

Clause 7. A lung cancer detection system according to clause 2, 3, 4, or 5 or any other clause wherein said antibodies are separate from each other allowing non-simultaneous application to a sample.

Clause 8. A lung cancer detection system according to clause 1, 2, or 5 or any other clause wherein said primary antibodies that specifically bind to squamous cell carcinoma (SCC) comprises at least one antibody selected from a group consisting of: anti-Desmoglein 3(anti-DSG-3) antibody, anti-CK5 antibody, anti-p63 antibody, anti-p40 antibody, and anti-TRIM29 antibody.

Clause 9. A lung cancer detection system according to clause 1, 3, or 4 or any other clause wherein said primary antibodies that specifically bind to adenocarcinoma (ADC) comprises at least one antibody selected from a group consisting of: anti-Napsin A antibody, anti-TTF-1 antibody, and anti-CK7 antibody.

Clause 10. A lung cancer detection system comprising a primary antibody combination selected from the group consisting of:
anti-DSG-3 antibody or fragment thereof, anti-CK5 antibody or fragment thereof, and anti-Napsin A antibody or fragment thereof;

anti-p40 antibody or fragment thereof, and anti-TTF-1 antibody or fragment thereof;

anti-DSG-3 antibody or fragment thereof, anti-p40 antibody or fragment thereof, and anti-Napsin A antibody or fragment thereof;

anti-DSG-3 antibody or fragment thereof, and anti-p40 antibody or fragment thereof;

anti-p40 antibody or fragment thereof, and anti-CK5 antibody or fragment thereof;

anti-CK7 antibody or fragment thereof, and anti-TRIM29 antibody or fragment thereof;

anti-DSG-3 antibody or fragment thereof, anti-CK5 antibody or fragment thereof, anti-Napsin A antibody or fragment thereof, and anti-TTF-1 antibody or fragment thereof;

anti-DSG-3 antibody or fragment thereof, anti-CK5 antibody or fragment thereof, anti-p40 antibody or fragment thereof, anti-Napsin A antibody or fragment thereof, and anti-TTF-1 antibody or fragment thereof;

anti-DSG-3 antibody or fragment thereof, anti-CK5 antibody or fragment thereof, and anti-p40 antibody or fragment thereof;

anti-DSG-3 mouse antibody or fragment thereof, anti-CK5 mouse antibody or fragment thereof, anti-Napsin A rabbit antibody or fragment thereof;

anti-p40 rabbit antibody or fragment thereof, and anti-TTF-1 mouse antibody or fragment thereof;

anti-DSG-3 mouse antibody or fragment thereof, anti-p40 mouse antibody or fragment thereof, and anti-Napsin A rabbit antibody or fragment thereof;

anti-DSG-3 mouse antibody or fragment thereof, and anti-p40 mouse antibody or fragment thereof;

anti-p40 mouse antibody or fragment thereof, and anti-CK5 rabbit antibody or fragment thereof;

anti-TRIM29 rabbit antibody or fragment thereof, and anti-CK7 mouse antibody or fragment thereof;

anti-DSG-3 mouse antibody or fragment thereof, anti-CK5 mouse antibody or fragment thereof, anti-Napsin A rabbit antibody or fragment thereof, and anti-TTF-1 mouse antibody or fragment thereof;

anti-DSG-3 mouse antibody or fragment thereof, anti-CK5 mouse antibody or fragment thereof, anti-p40 rabbit antibody or fragment thereof, anti-Napsin A rabbit antibody or fragment thereof, and anti-TTF-1 mouse antibody or fragment thereof;

anti-DSG-3 mouse antibody or fragment thereof, anti-CK5 mouse antibody or fragment thereof, and anti-p40 rabbit antibody or fragment thereof; and anti-DSG-3 mouse antibody or fragment thereof, and anti-p40 rabbit antibody or fragment thereof.

Clause 11. A lung cancer detection system according to clause 1, 2, 3, 4, 5, or 10 or any other clause wherein said primary antibodies are derived from a host species selected from a group consisting of mouse, rabbit, chicken, horse, rat, goat, sheep, and any combination thereof.

Clause 12. A lung cancer detection system according to claus 11 or any other clause wherein said primary antibodies are derived from the same host species.

Clause 13. A lung cancer detection system according to clause 11 or any other clause wherein said primary antibodies are derived from different host species.

Clause 14. A lung cancer detection system according to clause 1, 2, 3, 4, 5, or 10 or any other clause and further comprising at least one antibody-enzyme conjugate.

Clause 15. A lung cancer detection system according to clause 14 or any other clause and further comprising at least one chromogen.

Clause 16. A lung cancer detection system according to clause 14 or any other clause wherein said at least one antibody-enzyme conjugate comprises an antibody selected from a group consisting of anti-rabbit antibody, anti-mouse antibody, anti-chicken antibody, anti-horse antibody, anti-rat antibody, anti-goat antibody, anti-sheep antibody, and any combination thereof.

Clause 17. A lung cancer detection system according to clause 16 or any other clause wherein said at least one antibody-enzyme conjugate comprises an enzyme selected from a group consisting of horseradish peroxidase (HRP), alkaline phosphate (AP), glucose oxidase, β-galactosidase, and any combination thereof.

Clause 18. A lung cancer detection system according to clause 15 or any other clause wherein said at least one chromogen is selected from a group consisting of 3,3'-diaminobenzidine (DAB); Fast Red; 3-amino-9-ethylcarbazole (AEC); Fast Blue; 3,3',5,5'-tetramethylbenzidine (TMB); 5-Bromo-4-chloro-3-indolyl phosphate (BCIP); nitro blue tetrazolium (NBT); tetranitrobluetetrazolium (TNBT); New fuschin, 5-bromo-4-chloro-3-indolyl-β-D-galactopyranoside (X-Gal); 5-Bromo-3-indolyl β-D-galactopyranoside (Bluo-Gal); and any combination thereof.

Clause 19. A lung cancer detection system according to clause 1, 2, 3, 4, 5, or 10 or any other clause wherein said antibodies are selected from the group consisting of a polyclonal antibody and a monoclonal antibody.

Clause 20. A lung cancer detection system according to clause 14 or any other clause wherein an antibody of said at least one antibody-enzyme conjugate binds to said primary antibody.

Clause 21. A lung cancer detection system according to clause 14 or any other clause wherein an antibody of said at least one antibody-enzyme conjugate is derived from a different host species as said primary antibody.

Clause 22. A lung cancer detection system according to clause 1, 2, 3, 4, 5, or 10 or any other clause wherein said antibodies comprises isolated antibodies.

Clause 23. A lung cancer detection system according to clause 1, 2, 3, 4, 5, or 10 or any other clause wherein said fragment thereof comprises an antigen binding fragment thereof.

Clause 24. A lung cancer detection system according to clause 2 or 3 or any other clause and further comprising a single antibody-enzyme conjugate to said at least two primary antibodies.

Clause 25. A lung cancer detection system according to clause 24 wherein said single antibody-enzyme conjugate comprises an antibody selected from a group consisting of anti-rabbit antibody, anti-mouse antibody, anti-chicken antibody, anti-horse antibody, anti-rat antibody, anti-goat antibody, anti-sheep antibody, and any combination thereof; and comprises an enzyme selected from a group consisting of horseradish peroxidase (HRP), alkaline phosphate (AP), glucose oxidase, β-galactosidase, and any combination thereof.

Clause 26. A method for detecting lung cancer in a biological sample comprising the steps of:

contacting a biological sample with at least two primary antibodies or fragments thereof, wherein at least one primary antibody or fragment thereof is capable of specifically binding to squamous cell carcinoma (SCC) and forming at least one antigen-antibody complex; and wherein at least one primary antibody or fragment thereof is capable of specifically binding to adenocarcinoma (ADC) and forming at least one antigen-antibody complex; and detecting said antigen-antibody complexes.

Clause 27. A method for detecting lung cancer in a biological sample comprising the steps of:

contacting a biological sample with at least two primary antibodies or fragments thereof, wherein at least two of said primary antibodies are each capable of specifically binding to squamous cell carcinoma (SCC) and forming at least one antigen-antibody complex; and detecting said antigen-antibody complex.

Clause 28. A method for detecting lung cancer in a biological sample comprising the steps of:

contacting a biological sample with at least two primary antibodies or fragments thereof, wherein at least two of said primary antibodies are each capable of specifically binding to adenocarcinoma (ADC) and forming at least one antigen-antibody complex; and detecting said antigen-antibody complex.

Clause 29. A method for detecting lung cancer in a biological sample comprising the steps of:

contacting a biological sample with a primary antibody combination, and detecting said antigen-antibody complex, wherein said primary antibody combination is selected from a group consisting of:

anti-DSG-3 antibody or fragment thereof, anti-CK5 antibody or fragment thereof, and anti-Napsin A antibody or fragment thereof;

anti-p40 antibody or fragment thereof, and anti-TTF-1 antibody or fragment thereof;

anti-DSG-3 antibody or fragment thereof, anti-p40 antibody or fragment thereof, and anti-Napsin A antibody or fragment thereof;

anti-DSG-3 antibody or fragment thereof, and anti-p40 antibody or fragment thereof;

anti-p40 antibody or fragment thereof, and anti-CK5 antibody or fragment thereof;

anti-CK7 antibody or fragment thereof, and anti-TRIM29 antibody or fragment thereof;

anti-DSG-3 antibody or fragment thereof, anti-CK5 antibody or fragment thereof, anti-Napsin A antibody or fragment thereof, and anti-TTF-1 antibody or fragment thereof;

anti-DSG-3 antibody or fragment thereof, anti-CK5 antibody or fragment thereof, anti-p40 antibody or fragment thereof, anti-Napsin A antibody or fragment thereof, and anti-TTF-1 antibody or fragment thereof;

anti-DSG-3 antibody or fragment thereof, anti-CK5 antibody or fragment thereof, and anti-p40 antibody or fragment thereof;

anti-DSG-3 mouse antibody or fragment thereof, anti-CK5 mouse antibody or fragment thereof, anti-Napsin A rabbit antibody or fragment thereof;

anti-p40 rabbit antibody or fragment thereof, and anti-TTF-1 mouse antibody or fragment thereof;

anti-DSG-3 mouse antibody or fragment thereof, anti-p40 mouse antibody or fragment thereof, and anti-Napsin A rabbit antibody or fragment thereof;

anti-DSG-3 mouse antibody or fragment thereof, and anti-p40 mouse antibody or fragment thereof;

anti-p40 mouse antibody or fragment thereof, and anti-CK5 rabbit antibody or fragment thereof;

anti-TRIM29 rabbit antibody or fragment thereof, and anti-CK7 mouse antibody or fragment thereof;

anti-DSG-3 mouse antibody or fragment thereof, anti-CK5 mouse antibody or fragment thereof, anti-Napsin A rabbit antibody or fragment thereof, and anti-TTF-1 mouse antibody or fragment thereof;

anti-DSG-3 mouse antibody or fragment thereof, anti-CK5 mouse antibody or fragment thereof, anti-p40 rabbit antibody or fragment thereof, anti-Napsin A rabbit antibody or fragment thereof, and anti-TTF-1 mouse antibody or fragment thereof;

anti-DSG-3 mouse antibody or fragment thereof, anti-CK5 mouse antibody or fragment thereof, and anti-p40 rabbit antibody or fragment thereof; and anti-DSG-3 mouse antibody or fragment thereof, and anti-p40 rabbit antibody or fragment thereof.

Clause 30. A method for detecting lung cancer in a biological sample according to clause 26, 27, 28, or 29 or any other clause wherein said step of detecting antigen-antibody complexes comprises a step selected from a group consisting of: manually detecting, automatically detecting, image analysis detecting.

Clause 31. A method for detecting lung cancer in a biological sample according to clause 26, 27, 28, or 29 or any other clause wherein said step of contacting said biological sample with at least two primary antibodies or fragments thereof comprises the step of simultaneously contacting biological sample with at least two primary antibodies or fragments thereof.

Clause 32. A method for detecting lung cancer in a biological sample according to clause 26, 27, 28, or 29 or any other clause wherein said step of contacting said biological sample with at least two primary antibodies or fragments thereof comprises the step of separately contacting each of said at least two primary antibodies or fragments thereof with said biological sample.

Clause 33. A method for detecting lung cancer in a biological sample according to clause 26, 27, 28, or 29 or any other clause wherein said step of detecting said antigen-antibody complexes comprises the step of locating said antigen-antibody complexes in said biological sample.

Clause 34. A method for detecting lung cancer in a biological sample according to clause 27 or any other clause and further comprising at least one primary antibody capable of specifically binding to adenocarcinoma (ADC).

Clause 35. A method for detecting lung cancer in a biological sample according to clause 28 or any other clause and further comprising at least one primary antibody capable of specifically binding to squamous cell carcinoma (SCC).

Clause 36. A method for detecting lung cancer in a biological sample according to clause 26, 27, or 35 or any other clause wherein said primary antibody capable of specifically binding to squamous cell carcinoma (SCC) comprises at least one antibody selected from a group consisting of: anti-Desmoglein 3(anti-DSG-3) antibody, anti-CK5 antibody, anti-p63 antibody, anti-p40 antibody, and anti-TRIM29 antibody.

Clause 37. A method for detecting lung cancer in a biological sample according to clause 26, 28, or 34 or any other clause wherein said primary antibody capable of specifically binding to adenocarcinoma (ADC) comprises at least one antibody selected from a group consisting of: anti-Napsin A antibody, anti-TTF-1 antibody, and anti-CK7 antibody.

Clause 38. A method for detecting lung cancer in a biological sample according to clause 26, 27, 28, or 29 or any other clause wherein said primary antibodies are derived from a host species selected from a group consisting of mouse, rabbit, chicken, horse, rat, goat, sheep, and any combination thereof.

Clause 39. A method for detecting lung cancer in a biological sample according to clause 26, 27, 28, or 29 or any other clause wherein said primary antibodies are derived from the same host species.

Clause 40. A method for detecting lung cancer in a biological sample according to clause 26, 27, 28, or 29 or any other clause wherein said primary antibodies are derived from different host species.

Clause 41. A method for detecting lung cancer in a biological sample according to clause 26, 27, 28, 29, 34, or 35 or any other clause and further comprising the step of applying at least one antibody-enzyme conjugate capable of binding to at least one of said primary antibodies to said biological sample.

Clause 42. A method for detecting lung cancer in a biological sample according to clause 41 or any other clause and further comprising the step of applying at least one chromogen to said biological sample.

Clause 43. A method for detecting lung cancer in a biological sample according to clause 41 or any other clause wherein said at least one antibody-enzyme conjugate comprises an antibody selected from a group consisting of anti-rabbit antibody, anti-mouse antibody, anti-chicken antibody, anti-horse antibody, anti-rat antibody, anti-goat antibody, anti-sheep antibody, and any combination thereof.

Clause 44. A method for detecting lung cancer in a biological sample according to clause 43 or any other clause wherein said at least one antibody-enzyme conjugate comprises an enzyme selected from a group consisting of horseradish peroxidase (HRP), alkaline phosphate (AP), glucose oxidase, β-galactosidase, and any combination thereof.

Clause 45. A method for detecting lung cancer in a biological sample according to clause 42 or any other clause wherein said at least one chromogen is selected from a group consisting of 3,3'-diaminobenzidine (DAB); Fast Red; 3-amino-9-ethylcarbazole (AEC); Fast Blue; 3,3',5,5'-tetramethylbenzidine (TMB); 5-Bromo-4-chloro-3-indolyl phosphate (BCIP); nitro blue tetrazolium (NBT); tetranitrobluetetrazolium (TNBT); New fuschin, 5-bromo-4-chloro-3-indolyl-β-D-galactopyranoside (X-Gal); 5-Bromo-3-indolyl β-D-galactopyranoside (Bluo-Gal); and any combination thereof.

Clause 46. A method for detecting lung cancer in a biological sample according to clause 45 or any other clause and further comprising the step of producing at least one color stain on said biological sample.

Clause 47. A method for detecting lung cancer in a biological sample according to clause 26, 27, 28, 29, 34, or 35 or any other clause wherein said antibodies are selected from the group consisting of a polyclonal antibody and a monoclonal antibody.

Clause 48. A method for detecting lung cancer in a biological sample according to claim 41 or any other clause wherein said step of applying said at least one antibody-enzyme conjugate capable of binding to at least one of said primary antibodies comprises the step of applying at least one antibody-enzyme conjugate capable of binding to at least two of said primary antibodies.

Clause 49. A method for detecting lung cancer in a biological sample according to clause 41 or any other clause wherein said single antibody-enzyme conjugate comprises an antibody selected from a group consisting of anti-rabbit antibody, anti-mouse antibody, anti-chicken antibody, anti-horse antibody, anti-rat antibody, anti-goat antibody, anti-sheep antibody, and any combination thereof; and comprises an enzyme selected from a group consisting of horseradish peroxidase (HRP), alkaline phosphate (AP), glucose oxidase, β-galactosidase, and any combination thereof.

Clause 50. A diagnostic or prognostic test kit comprising:
the antibodies or fragments thereof according to clause 1, 2, 3, 4, or 5 or any other clause; and
an antibody detection element of said antibody or said fragment thereof when bound to an antigen.

Clause 51. Use of the antibodies or fragments thereof or composition according to any of clause 1-25 or any other clause to detect lung cancer.

Clause 52. Use of the antibodies or fragments thereof or composition according to any of clause 1-25 or any other clause to distinguish between squamous cell carcinoma (SCC) and adenocarcinoma (ADC).

Clause 53. Use of the antibodies or fragments thereof or composition according to any of clause 1-25 or any other clause to predict outcome of treatment of cancer.

Clause 54. Use of the antibodies or fragments thereof or composition according to any of clause 1-25 or any other clause to assess efficacy of treatment of cancer.

As can be easily understood from the foregoing, the basic concepts of the present invention may be embodied in a variety of ways. It involves both antibody techniques as well as devices to accomplish the appropriate antibody cocktail. In this application, the antibody cocktail techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detection" or "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below or in any list of References or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

I. U.S. Patent Documents

| Pat. No. | Kind Code | Issue Date | Name of Patentee or Applicant of cited Document |
|---|---|---|---|
| 8,603,765 | B2 | 2013-12-10 | Tacha |

II. U.S. Patent Application Publications

| Publication Number | Kind Code | Publication Date | Name of Patentee or Applicant of cited Document |
|---|---|---|---|
| 20120082999 | A1 | 2012-04-05 | Liao et al. |

III. Foreign Patent Documents

| Foreign Document Number | Country Code | Kind Code | Publication Date | Name of Patentee or Applicant of cited Document |
|---|---|---|---|---|
| 2012/154983 | WO | A2 | 2012-11-15 | Biocare Medical LLC |

IV. Non-Patent Literature Documents

Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162
Tacha D., et al. A 6-Antibody Panel for the Classification of Lung Adenocarcinoma Versus Squamous Cell Carcinoma, Appl Immunohistochem Mol Morphol Volume 20, Number 3, May 2012
Savci-Heijink C. D., et al. The role of desmoglein-3 in the diagnosis of squamous cell carcinoma of the lung. Am J Pathol. 2009; 174(5): 1629-1637
Ring B. Z., et al. A novel five-antibody immunohisto-chemical test for subclassification of lung carcinoma. Mod Pathol. 2009; 22(8): 1032-1043
Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 5/6. Am J Surg Pathol, 2011; 35(1): 15-25
Bishop J. A., p40 (ΔNp63) is superior to p63 for the diagnosis of pulmonary sauamous -continued cell carcinoma, Modern Pathology (2011), 1-11; republished 2012 Mar; 25(3): 405-15
Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. 2006 Feb 2; 6: 31
Hirsch F. R., et al. "The prognostic and predictive role of histology in advanced non-small cell lung cancer: a literature review, 2008 Dec; 3(12): 1468-81
Fukuoka J, et al. "Desmoglein 3 as a prognostic factor in lung cancer 2007 Feb; 38(2): 276-83
Lee J. G, et al. "Napsin A is an independent prognostic factor in surgically resected adenocarcinoma of the lung." 2012 Jul; 77(1): 156-61
Brown, et al. Tissue-Preserving Antibody Cocktails to Differentiate Primary Squamous Cell Carcinoma, Adenocarcinoma, and Small Cell Carcinoma of Lung", Arch Pathol Lab Med, Early Release Online, Jan. 4, 2013.
Brown, et al. "Tissue-Preserving Antibody Cocktails to Differentiate Primary Squamous Cell Carcinoma, Adenocarcinoma, and Small Cell Carcinoma of Lung", Arch Pathol Lab Med Vol 137, September 2013
van der Loos, CM. Immunoenzyme Multiple Staining Methods. 1999. BIOS Scientific Publishers; Oxford, UK.

Thus, the applicant(s) should be understood to have support to clauseand make a statement of invention to at least: i) each of the antibody devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent clauseor concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 5 or any other claim" or the like, it could be re-drafted as dependent on claim 1, claim 2, or even claim 7 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A lung cancer detection system comprising:
   a cocktail of two primary antibodies,
   wherein a first primary antibody of said cocktail comprises an anti-p40 mouse monoclonal antibody, clone BC28, which specifically binds to squamous cell carcinoma (SCC); and
   wherein a second primary antibody of said cocktail comprises an anti-TTF-1 mouse monoclonal antibody which specifically binds to adenocarcinoma (ADC).

2. A lung cancer detection system according to claim 1 and further comprising at least one antibody-enzyme conjugate.

3. A lung cancer detection system according to claim 2 and further comprising at least one chromogen.

4. A lung cancer detection system according to claim 2 wherein said at least one antibody-enzyme conjugate comprises an antibody selected from a group consisting of anti-rabbit antibody, anti-mouse antibody, anti-chicken antibody, anti-horse antibody, anti-rat antibody, anti-goat antibody, anti-sheep antibody, and any combination thereof.

5. A lung cancer detection system according to claim 4 wherein said at least one antibody-enzyme conjugate comprises an enzyme selected from a group consisting of horseradish peroxidase (HRP), alkaline phosphate (AP), glucose oxidase, β-galactosidase, and any combination thereof.

6. A lung cancer detection system according to claim 3 wherein said at least one chromogen is selected from a group consisting of 3,3'-diaminobenzidine (DAB); Fast Red; 3-amino-9-ethylcarbazole (AEC); Fast Blue; 3,3',5,5'-tetramethylbenzidine (TMB); 5-Bromo-4-chloro-3-indolyl phosphate (BCIP); nitro blue tetrazolium (NBT); tetranitrobluetetrazolium (TNBT); New fuschin, 5-bromo-4-chloro-3-indolyl-β-D-galactopyranoside (X-Gal); 5-Bromo-3-indolyl β-D-galactopyranoside (Bluo-Gal); and any combination thereof.

7. A lung cancer detection system according to claim 2 wherein an antibody of said at least one antibody-enzyme conjugate binds to at least one of said two primary antibodies.

* * * * *